US008703289B2

(12) United States Patent
Tamori et al.

(10) Patent No.: US 8,703,289 B2
(45) Date of Patent: Apr. 22, 2014

(54) ORGANIC POLYMER PARTICLES AND PROCESS FOR PRODUCING THE SAME, MAGNETIC PARTICLES FOR DIAGNOSTICS, CARBOXYL GROUP-CONTAINING PARTICLES AND PROCESS FOR PRODUCING THE SAME, AND PROBE-BOUND PARTICLES AND PROCESS FOR PRODUCING THE SAME

(75) Inventors: Kouji Tamori, Tsuchiura (JP); Tetsuo Fukuta, Tsuchiura (JP); Mitsuhiro Murata, Ushiku (JP); Masaru Ueno, Tsukuba (JP); Satoshi Katayose, Tsuchiura (JP); Eiji Takamoto, Tsuchiura (JP); Kiyoshi Kasai, Kameyama (JP)

(73) Assignee: JSR Corporation, Tokyo (JP)

( * ) Notice: Subject to any disclaimer, the term of this patent is extended or adjusted under 35 U.S.C. 154(b) by 1077 days.

(21) Appl. No.: 11/588,388

(22) Filed: Oct. 27, 2006

(65) Prior Publication Data
US 2007/0099814 A1 May 3, 2007

(30) Foreign Application Priority Data

| Nov. 1, 2005 | (JP) | 2005-318065 |
| Jan. 25, 2006 | (JP) | 2006-15994 |
| Feb. 24, 2006 | (JP) | 2006-48947 |
| Mar. 20, 2006 | (JP) | 2006-76085 |
| Mar. 27, 2006 | (JP) | 2006/85040 |

(51) Int. Cl.
*B32B 5/16* (2006.01)
*A61K 9/14* (2006.01)

(52) U.S. Cl.
USPC ............ 428/403; 424/489; 424/501; 428/407

(58) Field of Classification Search
USPC .......................... 428/403, 407; 424/489, 501
See application file for complete search history.

(56) References Cited

U.S. PATENT DOCUMENTS

| 4,336,173 | A | 6/1982 | Ugelstad | |
| 4,459,378 | A | 7/1984 | Ugelstad | |
| 5,091,206 | A | 2/1992 | Wang et al. | |
| 5,114,577 | A * | 5/1992 | Kusano et al. | 210/198.2 |
| 5,789,133 | A | 8/1998 | Yabuuchi et al. | |
| 6,605,404 | B2 * | 8/2003 | VanDusen et al. | 430/111.1 |
| 7,351,430 | B2 * | 4/2008 | St. John et al. | 424/489 |
| 7,713,627 | B2 * | 5/2010 | Tamori et al. | 428/407 |
| 2004/0018564 | A1 | 1/2004 | Kasai et al. | |
| 2005/0119761 | A1 | 6/2005 | Matsumoto | |
| 2006/0024845 | A1 | 2/2006 | Tanaka et al. | |
| 2006/0177943 | A1 | 8/2006 | Tanaka et al. | |
| 2007/0009441 | A1 * | 1/2007 | Erathodiyil et al. | 424/9.34 |

FOREIGN PATENT DOCUMENTS

| EP | 0 787 988 A2 | 8/1997 |
| EP | 1 036 836 A1 | 9/2000 |
| EP | 1 553 412 A1 | 7/2005 |
| EP | 1 564 555 A1 | 8/2005 |
| EP | 1 617 220 A1 | 1/2006 |
| EP | 1 650 565 A1 | 4/2006 |
| EP | 1 890 148 A1 * | 2/2008 |
| JP | 56-141559 | 11/1981 |
| JP | 57-24369 | 5/1982 |
| JP | 58-149910 | 9/1983 |
| JP | 59-232102 | 12/1984 |
| JP | 61-215602 | 9/1986 |
| JP | 61-215603 | 9/1986 |
| JP | 61-215604 | 9/1986 |
| JP | A-62-075267 | 4/1987 |
| JP | 04-156952 | 5/1992 |
| JP | 10-195099 | 7/1998 |
| JP | 10-270233 | 10/1998 |
| JP | 11-174057 | 7/1999 |
| JP | 2000-300283 | 10/2000 |
| JP | 2000-304749 | 11/2000 |
| JP | 2001-272406 | 10/2001 |
| JP | 2002-121549 | 4/2002 |
| JP | 2003-231648 | 8/2003 |
| JP | 2003-277455 | 10/2003 |
| JP | 2004-61301 | 2/2004 |
| JP | 2004-205481 | 7/2004 |
| JP | 2004-331953 | 11/2004 |
| JP | 2005-69926 | 3/2005 |
| JP | 2005-083904 | 3/2005 |
| JP | A-2005-083905 | 3/2005 |
| JP | 2005-148048 | 6/2005 |
| JP | 2005-232237 | 9/2005 |

(Continued)

OTHER PUBLICATIONS

Online machine translation of JP 2005-069926 (Mar. 17, 2005).*
U.S. Appl. No. 11/914,986, filed Nov. 20, 2007, Takahashi, et al.
U.S. Appl. No. 11/961,562, filed Dec. 20, 2007, Tamori, et al.
Lars H. Jansson, et al., "High Swelling of Latex Particles Without the Utilization of Swelling Agents", Journal of Polymer Science: Polymer Letters Edition, vol. 21, 1983, pp. 937-943.
U.S. Appl. No. 11/954,289, filed Dec. 12, 2007, Tamori, et al.
U.S. Appl. No. 12/529,824, filed Sep. 3, 2009, Katayose, et al.
Notice of Opposition issued Sep. 14, 2010, in European Patent Application No. 06122165.1-2102/1780544.
Notice of Opposition issued Nov. 3, 2010, in European Patent Application No. 07121917.4-2102/1890147.
Zhi-Ya Ma, et al., Synthesis of Monodisperse Nonporous Crosslinked poly(glycidyl methacrylate) Particles with Metal Affinity Ligands for Protein Adsorption, Polymer International, vol. 54, Jul. 15, 2005, 1502-1507.

(Continued)

Primary Examiner — Hoa (Holly) Le
(74) Attorney, Agent, or Firm — Oblon, Spivak, McClelland, Maier & Neustadt, L.L.P.

(57) ABSTRACT

The organic polymer particles comprise a carboxyl group and 2,3-dihydroxypropyl group, and the magnetic particles for diagnostics comprise fine magnetic material particles and a polymer part containing a hydrophilic polymer part and a crosslinked polymer part, a dry coating film obtained from a water dispersion thereof having a contact angle with water of 5° to 60°. The process for producing the carboxyl group-containing particles comprises a step of producing an ester bond by reacting a hydroxyl group in organic polymer particles having the hydroxyl group with a carboxylic anhydride. The organic polymer particles comprise a hydroxyl group originating from a 2,3-dihydroxypropyl group and a polyoxyethylene group.

10 Claims, No Drawings

(56) References Cited

FOREIGN PATENT DOCUMENTS

| JP | 2007-288133 | 11/2007 |
|---|---|---|
| JP | 4716034 | 11/2007 |
| WO | WO 2004/025297 A1 | 3/2004 |
| WO | WO 2004/040305 A1 | 5/2004 |
| WO | WO 2004/092732 A1 | 10/2004 |
| WO | WO 2005/015216 A1 | 2/2005 |

OTHER PUBLICATIONS

David L. Cocke, et al., "Interaction Between Poly(ethylene glycol) and Human Serum Albumin", Chem., Commun., 1997, pp. 2331-2332.
Harris J. Milton, et al., "Poly(ethylene glycol), Chemistry and Biological Applications", American Chemical Society, ISBN:0-8412-3537-6, 1997, pp. 5,6, 400 and 401.
U.S. Appl. No. 13/025,273, filed Feb. 11, 2011, Takahashi, et al.
U.S. Appl. No. 13/218,494, filed Aug. 26, 2011, Tamori, et al.
Office Action dated Jun. 1, 2011 (with/Partial English Translation).
Japanese Office Action in application No. 2006-085040 dated Sep. 7, 2011, with partial English translation.
Japanese Office Action in application No. 2006-048947 dated Aug. 10, 2011, with partial English translation.
U.S. Appl. No. 13/152,802, filed Jun. 3, 2011, Tamori, et al.
Japanese Office Action issued Feb. 15, 2012, in Japan Patent Application No. 2006-048947 (with Partial English Translation).
Communication of Summons to attend Oral proceedings pursuant to Rule 115(1) EPC dated Mar. 13, 2012.
Communication of Summons to attend Oral proceedings pursuant to Rule 115(1) EPC dated Mar. 27, 2012.
Official Communication from the Boards of Appeal issued Oct. 4, 2013, in European Patent No. EP 1780544.
"Chemistry of Synthetic examples of opposed patent" Publication: N/A, Document provided with Opposition on Oct. 4, 2013, 6 Pages.
"Dynabeads M-270 Carboxylic Acid product inserts" Dynal Biotech, Rev. No. 002, Apr. 2004, 5 Pages.
"Analysis of carboxyl groups of Dynabeads M-270 Carboxylic Acid" Publication: N/A, Document provided with Opposition on Oct. 4, 2013, 4 Pages.
"Analysis of the 2.3-propandiol group in Dynabeads M-270 Carboxylic acid and particles of D1, Example 6" Publication: N/A, Document provided with Opposition on Oct. 4, 2013, 2 Pages.
J.F. O'Dea, et al. "The Estimation of Small Amounts of Formaldehyde Liberated during the Oxidation of Carbohydrates and other Substances with Periodate" Biochemical Journal, Apr. 7, 2953, pp. 580-586.
Igor A Kozlov, et al, "Sythesis of Solid-Supported Mirror-Image Sugars: A Novel Method for Selecting Receptors for Cellular-Surface Carbohydrates" Chembiochem 2001, vol. 2, Oct. 1, 2001, pp. 741-746.
Magdalena Gabig-Ciminska, et al, "Detection of bacteriophage infection and prophage induction in bacterial cultures by means of electric DNA chips" Analytical Biochemistry 324, Jan. 1, 2004, pp. 84-91.
Kim Bundvig Barken, et al. "Effect of unlabeled helper probes on detection of an RNA target by bead-based sandwich hybridization" BioTechniques, vol. 36, No. 1, Jan. 1, 2004, pp. 124-132.
Magdalena Gabig-Ciminska, et al, "Identification of pathogenic microbial cells and spores by electrochemical detection on a biochip" Microbial Cell Factories, Apr. 16, 2004, 11 Pages.
"Invoice/purchase order re Dynabeads M-270 Carboxylic Acid," Woongbee Meditech No. 4494, Aug. 22, 2013.
"CLEIA data for organic particles prepared with different antibody binding protocols" Publication: N/A, Document provided with Opposition on Oct. 4, 2013, 5 Pages.
Paul C. Hiemenz , "Scope and Variables, The Importance of Small Particles," Principles of Colloid and Surface Chemistry, $2^{nd}$ Edition, 1986, pp. Cover, 4-10.
ChemSpider entry for 2,2 Bis[4-glycidyloxy)phenyl]propane, obtained at http://www.chemspider.com/Chemical-Structure.2199.html?rid=baac0ab6-ceb8-4122-9d6a-783e7c930095 on Oct. 8, 2013.
Official Communication from the Boards of Appeal dated Nov. 13, 2013, in European Patent No. 1 890 147.

\* cited by examiner

ORGANIC POLYMER PARTICLES AND PROCESS FOR PRODUCING THE SAME, MAGNETIC PARTICLES FOR DIAGNOSTICS, CARBOXYL GROUP-CONTAINING PARTICLES AND PROCESS FOR PRODUCING THE SAME, AND PROBE-BOUND PARTICLES AND PROCESS FOR PRODUCING THE SAME

Japanese Patent Application No. 2005-318065 filed on Nov. 1, 2005, Japanese Patent Application No. 2006-15994 filed on Jan. 25, 2006, Japanese Patent Application No. 2006-48947 filed on Feb. 24, 2006, Japanese Patent Application No. 2006-76085 filed on Mar. 20, 2006, and Japanese Patent Application No. 2006-85040 filed on Mar. 27, 2006 are hereby incorporated by reference in their entirety.

BACKGROUND OF THE INVENTION

The present invention relates to organic polymer particles and a process for producing the same, magnetic particles for diagnostics, and carboxyl group-containing particles and a process for producing the same.

The invention further relates to probe-bound particles comprising the organic polymer particles with a probe bound therewith and a process for producing the same.

Organic polymer particles and magnetic particles are used as a reaction solid phase of a diagnostic agent using an antigen-antibody reaction in order to detect substances to be examined such as infections, cancer markers, hormones, and the like. In such a diagnostic agent, a probe (primary probe) for inspecting an antibody or an antigen is immobilized on particles. A substance to be inspected in a sample reacts with a second inspection probe after having been caught by the particles via the primary probe. The second inspection probe (secondary probe) is labeled with a fluorescent substance or an enzyme, whereby the target substance is detected by fluorescence or by an enzyme reaction.

In recent years, due to a demand for an increase in the inspection sensitivity for early detection of diseases, an increase in sensitivity of a diagnostic agent has been an important subject. In order to increase sensitivity of diagnostic agents using magnetic particles, a method of using enzyme coloring as a detecting means is being replaced by a method of using fluorescence or chemiluminescence, both of which ensure higher sensitivity.

Development of these detection techniques are said to have reached a level in which a one molecule-detection target can be theoretically detected. In practice, however, sensitivity is still insufficient. One reason for the insufficient sensitivity is non-specific adsorption of secondary probes and impurities onto the surface of particles. For example, even if a technique that can theoretically detect a one molecule-detection target is used, detection of the one molecule is impossible if several molecules of a secondary probe are non-specifically adsorbed onto the surface of the particles. For this reason, a technique for controlling non-specific adsorption onto the particle surface of substance used for inspection is strongly demanded.

A blocking method has been used for controlling such non-specific adsorption. In the blocking method, after immobilizing a primary probe on the particles, the particle surface is covered with a blocking agent such as albumin or skim milk with minimal adsorptivity of a secondary probe, impurities, and the like. However, some blocking agents may not exhibit a sufficient effect of covering. Other blocking agents, which are biological substances, exhibit only poor quality stability. In some cases, a sufficient effect of controlling non-specific adsorption cannot be obtained even if the particle surface is adequately covered with a blocking agent, because the blocking agent loses its effect over time due to denaturing and the like.

In order to solve the problem of non-specific adsorption, a method of introducing a hydrophilic polymer onto the surface of a substrate for immunoassay represented by a 96-well plate has been proposed (JP-A-1-174057, JP-A-2000-304749, and JP-A-2001-272406). However, because the area available for immobilizing a primary probe is limited and the reaction of a primary probe with the target substance to be detected is a solid-liquid reaction, such an immunoassay substrate utilizing a plane has problems of poor efficiency of an antigen-antibody reaction, a long period of time required for inspection, and the like.

Furthermore, as countermeasures for decreasing non-specific adsorption, microspheres made from organic polymer particles of a styrene-glycidyl methacrylate copolymer and the like and a physiological active substance bonded to the organic polymer particles via a spacer (JP-A-10-195099, JP-A-2000-300283, WO 04/025297), organic polymer particles with a hydrophilic spacer introduced on the particle surface (JP-A-2004-331953, WO 04/040305), and the like have been proposed. These organic polymer particles, however, exhibited neither a sufficient effect of reducing non-specific adsorption nor sufficient immunoassay sensitivity.

The present inventors have proposed magnetic particles for immunoassay exhibiting almost no non-specific adsorption, the particles having hydrophilic monomers such as hydroxyalkyl (meth)acrylate, alkoxyalkyl (meth)acrylate, polyoxyalkylene ($C_2$-$C_4$) group-containing (meth)acrylate, epoxy group-containing (meth)acrylate, phosphorylcholine-analogous group-containing monomers, and the like copolymerized on the surface (JP-A-2005-69926). However, development of particles for immunoassay exhibiting higher sensitivity have been desired. If a large amount of hydrophilic functional groups are introduced in order to decrease non-specific adsorption, the viscosity of aggregates of magnetic particles (hereinafter referred to as "pellets") after magnetic separation unduly decreases and magnetic particles may migrate into the supernatant solution which is removed after the magnetic separation.

In addition, when a probe (a primary probe) for detecting proteins, such as an antibody or an antigen, and nucleic acid is bound to the particle surface, the particles may aggregate during the reaction.

SUMMARY

A first object of the invention is to provide organic polymer particles easily bound to a probe (a primary probe) for detecting proteins, such as an antibody or an antigen, nucleic acid, and the like, while exhibiting low non-specific adsorption, a process for producing such organic polymer particles, and probe-bound particles made from the organic polymer particles with a probe bonded thereto.

A second object of the invention is to provide magnetic particles for diagnosis which exhibit low non-specific adsorption and of which the pellets after magnetic separation have an appropriate viscosity.

A third object of the invention is to provide carboxyl group-containing particles exhibiting least non-specific adsorption, high sensitivity, and low noise and a process for producing the same.

In addition, a fourth object of the invention is to provide organic polymer particles exhibiting excellent dispersibility when bound to a probe (a primary probe) for detecting proteins, such as an antibody or an antigen, nucleic acid, and the like, while exhibiting least non-specific adsorption, a process for producing such organic polymer particles, organic polymer particles for binding a probe, a process for producing the same, probe-bound particles made of the organic polymer particles with a probe bonded thereto, and a process for producing the same.

In order to achieve the above first object, the inventors have conducted extensive studies and found that non-specific adsorption on polymer particles having two specific types of functional groups is very small and that probe-bound particles exhibiting outstandingly high sensitivity in the field of biochemical and medical products can be obtained by using the organic polymer particles. These findings have led to the completion of the invention. According to the invention, the following organic polymer particles, processes for producing the same, and probe-bound particles can be provided.

Organic polymer particles in one aspect of the invention have a carboxyl group and 2,3-dihydroxypropyl group.

The organic polymer particles may contain superparamagnetic fine particles. In this instance, the organic polymer particles may comprise nuclear particles, a magnetic material layer containing the superparamagnetic fine particles provided in the outer layer of the nuclear particles, and a polymer part having a carboxyl group and 2,3-dihydroxypropyl group provided in the outer layer of the magnetic material layer.

The probe-bound particles of one aspect of the invention may comprise the organic polymer particles and a probe bound with the organic polymer particles.

The process for producing the organic polymer particles having a carboxyl group and 2,3-dihydroxypropyl group of one aspect comprises a step of forming a polymer part by polymerizing a monomer part which contains a monomer (A) producing a carboxyl group by hydrolysis and a step of hydrolyzing the polymer part.

In this process, the monomer part may further comprise a monomer (B) producing a 2,3-dihydroxypropyl group by hydrolysis.

The process for producing the organic polymer particles having a carboxyl group and 2,3-dihydroxypropyl group of one aspect comprises a step of forming a polymer part by polymerizing a monomer part which contains a monomer (B) producing a 2,3-dihydroxypropyl group by hydrolysis and a step of hydrolyzing the polymer part.

In this process, the monomer part may further comprise a crosslinkable monomer (C).

In this process, the monomer part may comprise 5 to 40 parts by weight of the monomer (A), 40 to 95 parts by weight of the monomer (B) producing a 2,3-dihydroxypropyl group by hydrolysis, 0 to 30 parts by weight of the crosslinkable monomer (C), and 0 to 55 parts by weight of other monomers (D).

Due to the low non-specific adsorption properties, the organic polymer particles are suitable as organic polymer particles for biochemical inspections exhibiting outstandingly high sensitivity in the field of biochemical and medical products. The above probe-bound particles also exhibit outstandingly high sensitivity in the field of biochemical and medical products and can provide a high S/N ratio as a biochemical inspection material due to the low non-specific adsorption.

In order to achieve the above second object, the inventors have specified a composition of magnetic particles and found that if the composition is designed so that the contact angle of a dry coating film obtained from a water dispersion of the magnetic particles and water may fall in a specific range, small non-specific adsorption and moderate viscosity of pellets after magnetic separation can be satisfied at the same time, leading to completion of the invention. The following magnetic particles for diagnostics can be provided by the invention.

In one aspect, the magnetic particles for diagnostics of the invention comprise fine magnetic material particles and a polymer part containing a hydrophilic polymer part and a crosslinked polymer part, a dry coating film obtained from a water dispersion thereof having a contact angle with water of 5° to 60°.

Here, the hydrophilic polymer part can be a crosslinked polymer part at the same time, or a hydrophilic polymer part and a crosslinked polymer part may be present separately.

In the above-mentioned magnetic particles for diagnostics, the polymer part can be obtained by polymerizing the monomer part containing a hydrophilic monomer and a crosslinkable monomer.

The hydrophilic polymer part is obtained from the hydrophilic monomer by polymerization of the monomer part and the crosslinked polymer part can be obtained from the crosslinkable monomer by polymerization of the monomer part.

Here, the hydrophilic monomer can be the crosslinkable monomer at the same time, or a hydrophilic monomer and a crosslinkable monomer may be used separately.

In the above magnetic particles for diagnostics, the polymer part comprises nuclear particles and a coating layer and the above fine magnetic material particles form a magnetic material layer, the magnetic material layer being present on the outside of the nuclear particles and the coating layer being present on the outside of the magnetic material layer.

In this instance, the above coating layer contains the above hydrophilic polymer part, the above hydrophilic polymer part has an alcoholic hydroxyl group, and the above dry coating film has a contact angle with water of 10° to 30°. Here, the hydrophilic polymer part may have a 2,3-dihydroxypropyl group.

In this instance, the above hydrophilic polymer part has a carboxyl group, the above coating layer contains the above hydrophilic polymer part, and the above dry coating film has a contact angle with water of 20° to 40°.

According to this aspect, the above magnetic particles for diagnostics comprising the fine magnetic material particles and the polymer part containing, a hydrophilic polymer part, and a crosslinked polymer part is designed so that the contact angle of a dry coating film obtained from a water dispersion of the magnetic particles and water may fall in a specific range, whereby small non-specific adsorption and moderate viscosity of pellets after magnetic separation can be satisfied at the same time.

In order to achieve the above third object, the inventors have conducted extensive studies and found that carboxyl group-containing particles obtained from organic polymer particles having a hydroxyl group by reacting the hydroxyl group with an carboxylic anhydride to form an ester bond exhibit very low non-specific adsorption and outstandingly high sensitivity in the field of biochemical and medical products, leading to the completion of the invention.

The process for producing the carboxyl group-containing particles of one aspect comprises a step of producing an ester bond by reacting a hydroxyl group in organic polymer particles having the hydroxyl group with a carboxylic anhydride.

The process for producing the carboxyl group-containing particles of one aspect comprises a step of producing an ester bond by reacting a hydroxyl group originating from a 2,3- dihydroxypropyl group in organic polymer particles having the 2,3-dihydroxypropyl group with a carboxylic anhydride.

In the above process for producing the carboxyl group-containing particles, the above carboxylic anhydride is a polyvalent carboxylic anhydride and the above step of producing an ester bond may be a step of producing an ester bond and a carboxyl group.

In the above process for producing the carboxyl group-containing particles, the organic polymer particles may contain superparamagnetic fine particles.

The carboxyl group-containing particles of one aspect comprise mother particles containing nuclear particles and a magnetic material layer of superparamagnetic fine particles formed on the surface of the nuclear particles and a polymer part of crosslinked polymer covering the mother particles.

In the above carboxyl group-containing particles, the polymer part may contain an ester bond and a functional group containing a carboxyl group.

According to the above process for producing carboxyl group-containing particles, particles exhibiting only low non-specific adsorption, outstandingly high sensitivity in the field of biochemical and medical products, and a high S/N ratio as a biochemical inspection material can be obtained.

When the carboxyl group-containing particles obtained by the above process are used as, for example, a diagnostic agent utilizing an antigen-antibody reaction, the particles can exhibit outstandingly high sensitivity and low noise.

In order to achieve the above fourth object, the inventors have conducted extensive studies and found that polymer particles having two specific types of functional groups excel in dispersibility and that probe-bound particles exhibiting outstandingly high sensitivity and low noise in the field of biochemical and medical products can be obtained by using the organic polymer particles, leading to completion of the invention. According to the invention, the following organic polymer particles, organic polymer particles for probe binding, probe-bound particles, and processes for producing these particles can be provided.

Organic polymer particles of one aspect of the invention have a hydroxyl group originating from a 2,3-dihydroxypropyl group and a polyoxyethylene group.

Here, "hydroxyl group originating from a 2,3-dihydroxypropyl group" refers to both hydroxyl groups possessed by the 2,3-dihydroxypropyl group or, when either one of the hydroxyl groups is tosylated as described later, the remaining other hydroxyl group. In the latter case, it is sufficient that part of the hydroxyl groups among the hydroxyl groups of the 2,3-dihydroxypropyl groups in the organic polymer particles are not tosylated. The organic polymer particles may contain superparamagnetic fine particles.

In this instance, the organic polymer particles may comprise nuclear particles, a magnetic material layer containing the superparamagnetic fine particles provided in the outer layer of the nuclear particles, and a polymer part having a hydroxyl group originating from the 2,3-dihydroxypropyl group and a polyoxyethylene group provided in the outer layer of the magnetic material layer.

The organic polymer particles may contain a tosyl group.

The probe-bound particles for probe-binding of one aspect contain having a hydroxyl group originating from a 2,3-dihydroxypropyl group, a polyoxyethylene group, and a tosyl group. In the invention, "tosyl group" refers to "p-toluenesulfonyl group" and "tosylate" refers to converting a hydroxyl group into a "p-toluenesulfonyl group".

The probe-bound particles for probe-binding of one aspect comprise the above organic polymer particles bound with a probe.

The process for producing the organic polymer particles having a hydroxyl group originating from a 2,3-dihydroxypropyl group and a polyoxyethylene group of one aspect comprises a step of forming a polymer part by polymerizing a monomer part which contains a monomer (A) having a polyoxyethylene group.

The process for producing the organic polymer particles having a hydroxyl group originating from a 2,3-dihydroxypropyl group and a polyoxyethylene group of one aspect comprises a step of forming a polymer part by polymerizing a monomer part in the presence of a reactive emulsifier (R) having a polyoxyethylene group.

In the above process, the monomer part may further comprise a monomer (B) producing a 2,3-dihydroxypropyl group by hydrolysis and the process may further comprise a step of hydrolyzing the polymer part.

The process for producing the organic polymer particles of one aspect comprises a step of binding a modifier (M) having a polyoxyethylene group with organic polymer particles having a 2,3-dihydroxypropyl group.

In this instance, the process may further comprise a step of forming the above organic polymer particles having a 2,3-dihydroxypropyl group by polymerizing a monomer part containing a monomer (B) producing a 2,3-dihydroxypropyl group by hydrolysis to obtain particles having a polymer part and hydrolyzing this polymer part.

The process for producing organic polymer particles for probe binding of one aspect of the invention comprises a step of tosylating the organic polymer particles.

The process for producing the probe-bound particles of one aspect of the invention comprises a step of binding a probe with the organic polymer particles for probe binding.

The organic polymer particles are suitable as organic polymer particles for biochemical inspections due to excellent dispersibility during probe binding. and capability of exhibiting outstandingly high sensitivity and low noise in the field of biochemical and medical products due to the low non-specific adsorption properties.

The above organic polymer particles for probe-biding have excellent probe-bindability and can easily bind with a probe.

In addition, the above probe-bound particles exhibit outstandingly high sensitivity and low noise in the field of biochemical and medical products and can provide a high S/N ratio as a biochemical inspection material due to the low non-specific adsorption.

DETAILED DESCRIPTION OF THE EMBODIMENT

1. First Embodiment 1.1. Organic Polymer Particles

The organic polymer particles of one embodiment of the invention have a carboxyl group and a 2,3-dihydroxypropyl group. At least the surface of the organic polymer particles of this embodiment comprises a polymer part, for example, and at least the surface of the polymer part may have a carboxyl group and a 2,3-dihydroxypropyl group. In this instance, the polymer part may be formed by copolymerizing a monomer part containing a monomer having a carboxyl group and a monomer having a 2,3-dihydroxypropyl group or may be formed by copolymerizing a monomer part containing a monomer producing a carboxyl group by hydrolysis and a monomer producing a 2,3-dihydroxypropyl group by hydrolysis, followed by hydrolysis of the resulting copolymer. The polymer part may also be formed by copolymerizing a monomer part containing a monomer having a carboxyl group and a monomer producing a 2,3-dihydroxypropyl group by hydrolysis, followed by hydrolysis of the resulting copolymer, or by copolymerizing a monomer part containing a monomer producing a carboxyl group by hydrolysis and a monomer having a 2,3-dihydroxypropyl group, followed by hydrolysis of the resulting copolymer.

Either the entirety of the organic polymer particles of this embodiment may consist of a polymer part or the organic polymer particles may have a core-shell structure, with the shell being formed of a polymer part.

In the organic polymer particles of this embodiment, the carboxyl group is a factor for accelerating binding with a probe for inspection (a primary probe) by known activation by means of esterification or amidation using a water-soluble carbodiimide and the like. The primary probe and the method for binding will be described later.

In the organic polymer particles of this embodiment, the amount of the carboxyl group per the amount of solid components of the particles is preferably from 1 to 300 µmol/g, more preferably from 5 to 200 µmol/g, and most preferably from 10 to 100 µmol/g. If the amount of the carboxyl group is less than 1 µmol/g, binding of a primary probe may be difficult; if more than 300 µmol/g, on the other hand, non-specific adsorption of proteins and nucleic acids may increase. The hydrogen ion of the carboxyl group may be replaced by a cation such as a sodium ion, a potassium ion, or an ammonium ion.

In the organic polymer particles of this embodiment, the 2,3-dihydroxypropyl group is a factor for exhibiting low non-specific adsorption and high sensitivity. The amount of the 2,3-dihydroxypropyl group per the amount of solid components in the organic polymer particles is preferably 10 µmol/g or more, more preferably 50 µmol/g or more, and most preferably 100 µmol/g or more. If the amount of the 2,3-dihydroxypropyl group is less than 10 µmol/g, non-specific adsorption of proteins and nucleic acids may increase.

The number average particle diameter (hereinafter referred to simply as "particle diameter") of the organic polymer particles of this embodiment is preferably from 0.1 to 15 µm, more preferably from 0.3 to 10 µm, and most preferably from 1 to 10 µm. The particle diameter can be determined by the laser diffraction-scattering method. If the particle diameter is less than 0.1 µm, it takes a long time for separation using centrifugation and the like, resulting in insufficient separation of particles from a washing solvent such as water. This makes it difficult to sufficiently remove molecules other than target molecules (e.g. biological-related substances such as proteins and nucleic acids), giving rise to inadequate purification in some cases. On the other hand, if the particle diameter is more than 15 µm, the sensitivity may be impaired as a result of a decrease in the amount of captured physiologically active substances due to a small specific surface area.

The organic polymer particles of this embodiment are usually used by dispersing in an appropriate dispersion medium. A dispersion medium not dissolving the organic polymer particles or not swelling the organic polymer particles are preferably used as the dispersion medium. An aqueous medium can be given as a preferable dispersion medium. The aqueous medium here refers to water or a mixture of water and an organic solvent miscible with water (e.g. alcohols, alkylene glycol derivatives, etc.).

The contact angle of a dry coating film, which is made from a water dispersion of the organic polymer particles of this embodiment, with water is preferably 40° or less, more preferably 30° or less, and most preferably from 10° to 25°.

The dry coating film made from the water dispersion of the organic polymer particles can be obtained by preparing a water dispersion by dispersing 50 mg of the particles in 0.2 ml of purified water, applying this water dispersion to a flat and smooth substrate such as a glass slide using an applicator or the like, and drying the coating at a humidity of 40% and a temperature of 25° C. for 24 hours. The contact angle of the dry coating film with water can be determined by dripping about 1 µl of water on the dry coating film, immediately acquiring the image data from the horizontal direction using a camera, and measuring the angle between the outline of the water drop and the horizon of the coating film, assuming that the outline of the water drop is a part of a circle's perimeter. Low non-specific adsorption and high sensitivity can be ensured at the same time by having the contact angle of a dry coating film made from a water dispersion of the organic polymer particles of this embodiment with water in the above ranges.

The contact angle of a dry coating film made from a water dispersion of the organic polymer particles of this embodiment with water can be adjusted by varying the types and amounts of the monomers (A) to (D) which will be described later.

1.2. Production of Organic Polymer Particles 1.2.1. Composition of Monomer Part

The organic polymer particles of this embodiment are produced by forming a polymer part obtained by copolymerizing a monomer part at least on the surface. Each of the monomers for forming the monomer part will now be described.

1.2.1-1. Monomer (A)

The organic polymer particles of this embodiment are preferably formed by hydrolyzing particles comprising a polymer part obtained by copolymerizing a monomer part containing a monomer (A) producing a carboxyl group by hydrolysis on at least the surface. By using the monomer (A) producing a carboxyl group by hydrolysis in the above copolymerization, a carboxyl group can be uniformly introduced into the polymer part as compared with using a monomer having a carboxyl group before copolymerization, whereby non-specific adsorption of proteins and nucleic acids can be reduced.

When the monomer part further comprises a monomer (B) producing a 2,3-dihydroxypropyl group by hydrolysis, that is, when a monomer part further comprising the later-described monomer (B) producing a 2,3-dihydroxypropyl group by hydrolysis is copolymerized, hydrolysis of the monomer (B) before and during polymerization can be prevented. The following monomers (A) to (D) of this embodiment are preferably radically polymerizable monomers.

As the monomer (A) producing a carboxyl group by hydrolysis (hereinafter also referred to as "monomer (A)"), monomers in which the carboxyl group is protected by a known protecting group, for example, (A-1) an ester monomer in which the carboxyl group of a monomer having a carboxyl group is protected by a tertiary alcohol, (A-2) a cyclic ester monomer obtained by internal condensation of a monomer having a carboxyl group and a hydroxyl group in one molecule, (A-3) an acid anhydride of a monomer having a carboxyl group, and the like can be given.

As specific examples of the (A-1) ester monomer in which the carboxyl group is protected by an alcohol, t-butyl (meth)acrylate, 1-methylcyclopentyl (meth)acrylate, 1-ethylcyclopentyl (meth)acrylate, 1-methylcyclohexyl (meth)acrylate, 1-ethylcyclohexyl (meth)acrylate, 2-methyladamantan-2-yl (meth)acrylate, 2-ethyladamantan-2-yl (meth)acrylate, tetrahydrofuranyl (meth)acrylate, tetrahydropyranyl (meth)acrylate, and the like can be given.

As specific examples of the (A-2) cyclic ester monomer, α-acryloyloxy-γ-butyrolactone, α-methacryloyloxy-γ-butyrolactone, α-acryloyloxy-β,β-dimethyl-γ-butyrolactone, α-methacryloyloxy-ββ-dimethyl-γ-butyrolactone, α-acryloyloxy-αmethyl-γ-butyrolactone, α-methacryloyloxy-α-methyl-γ-butyrolactone, and the like can be given.

As specific examples of the (A-3) acid anhydride of a monomer, maleic anhydride, itaconic anhydride, and the like can be given.

Although the hydrolysis conditions of functional groups originating from monomer (A) vary according to the type of the monomer (A), particles dispersed in water are usually stirred from several hours to several tens of hours while heating and using an acid or a base as a catalyst to effect hydrolysis. As the catalyst, an acid catalyst is preferably used when the (A-1) ester monomer in which the carboxyl group is protected by a tertiary alcohol is used, and a base is preferably used when the (A-2) cyclic ester monomer and the (A-3) acid anhydride of a monomer are used.

In the hydrolysis of the functional groups originating from the monomer (A), not all of the functional groups of the copolymer need to be hydrolyzed as long as storage stability and the like are not hindered. Although the functional groups originating from the monomer (A) are usually the hydrolyzed after polymerization of the monomer part, a portion of the functional groups may be hydrolyzed during polymerization.

The monomer (A) is used in the monomer part preferably in an amount from 5 to 40 wt % and particularly preferably from 10 to 30 wt % for 100 wt % of the monomer part. If the amount of the monomer (A) in the monomer part is less than 5 wt %, binding of the primary probe may become difficult, and if the amount of the monomer (A) exceeds 40 wt %, non-specific adsorption may increase.

1.2.1-2. Monomer (B)

The organic polymer particles of this embodiment are preferably formed by hydrolyzing particles comprising a polymer part obtained by copolymerizing a monomer part containing a monomer (B) producing a 2,3-dihydroxypropyl group by hydrolysis on at least the surface. Specifically, in this instance, the monomer part further comprises a monomer (B) which produces a 2,3-dihydroxypropyl group by hydrolysis. In the above copolymerization, a larger amount of the 2,3-dihydroxypropyl group can be stably introduced into the polymer part by using the monomer (B) which produces a 2,3-dihydroxypropyl group by hydrolysis as compared with the case in which a monomer (B) having a 2,3-dihydroxypropyl group before copolymerization is used, whereby polymerization stability can be improved.

As the monomer (B) producing a 2,3-dihydroxypropyl group by hydrolysis (hereinafter also referred to as "monomer (B)"), monomers in which the hydroxyl group is protected by a known protecting group, for example, (B-1) a monomer having a 2,3-epoxypropyl group, (B-2) a monomer obtained by acetalating a 2,3-dihydroxypropyl group, (B-3) a monomer obtained by silylating a 2,3-dihydroxypropyl group, and the like can be given.

As specific examples of the (B-1) monomer having a 2,3-epoxypropyl group, glycidyl (meth)acrylate, allyl glycidyl ether, and the like can be given.

As specific examples of the (B-2) monomer obtained by acetalating a 2,3-dihydroxypropyl group, 1,3-dioxolan-2-on-4-ylmethyl (meth)acrylate, 1,3-dioxolane-2,2-dimethyl-4-ylmethyl (meth)acrylate, and the like can be given.

As specific examples of the (B-3) monomer obtained by silylating a 2,3-dihydroxypropyl group, di(t-butyl)silylated compound of 2,3-dihydroxypropyl (meth)acrylate, di(trimethylsilyl)ated compound of 2,3-dihydroxypropyl (meth)acrylate, and the like can be given.

Although the hydrolysis conditions of functional groups originating from monomer (B) vary according to the type of the monomer (B), particles dispersed in water are usually stirred from several hours to several tens of hours while heating and using an acid, a base, or a fluoride salt as a catalyst to effect hydrolysis. In the hydrolysis of the functional groups originating from the monomer (B), not all of the functional groups of the copolymer need to be hydrolyzed as long as storage stability and the like are not hindered. Although the functional groups originating from the monomer (B) are usually the hydrolyzed after polymerization of the monomer part, a portion of the functional groups may be hydrolyzed during polymerization.

The monomer (B) is used in the monomer part preferably in an amount from 40 to 95 wt % and particularly preferably from 50 to 90 wt % for 100 wt % of the monomer part. If the amount of the monomer (B) in the monomer part is less than 40 wt %, non-specific adsorption may increase, and if the amount of the monomer (B) exceeds 95 wt %, binding of the primary probe may become difficult.

1.2.1-3. Crosslinkable Monomer (C)

The organic polymer particles of this embodiment preferably have a particle surface obtained by copolymerizing a crosslinkable monomer (C). In this instance, the monomer part further comprises a crosslinkable monomer (C).

The crosslinkable monomer (C) (hereinafter also referred to as "monomer (C)") is a monomer which can be copolymerized with the monomer (A), monomer (B), and the like and possesses two or more radically polymerizable unsaturated bonds in one molecule. As examples of the crosslinkable monomers, polyfunctional (meth)acrylates such as ethylene glycol diacrylate, ethylene glycol dimethacrylate, trimethylolpropane triacrylate, trimethylolpropane trimethacrylate, pentaerythritol triacrylate, pentaerythritol trimethacrylate, dipentaerythritol hexacrylate, and dipentaerythritol hexamethacrylate; conjugated diolefins such as butadiene and isoprene; divinylbenzene, diallyl phthalate, allyl acrylate, allyl methacrylate, and the like can be given. As further examples of the crosslinkable monomers, hydrophilic monomers such as polyethylene glycol diacrylate, polyethylene glycol dimethacrylate, and poly(meth)acrylates of polyvinyl alcohol can be given.

The amount of the crosslinkable monomer (C) is preferably from 0 to 30 wt % and particularly preferably from 5 to 20 wt % for 100 wt % of the copolymer. If the amount of the monomer (C) in the copolymer exceeds 30 wt %, the particles become porous, possibly causing non-specific adsorption to increase.

1.2.1-4. Other Monomers (D)

The organic polymer particles of this embodiment may have a particle surface obtained by copolymerizing monomers (D) other than the above monomers (A) to (C) (other monomers (D)). As examples of the other monomers (D), (meth)acrylates having a hydrophilic functional group such as 2-hydroxyethyl acrylate, 2-hydroxyethyl methacrylate, methoxyethyl acrylate, methoxyethyl methacrylate, polyethylene glycol monoacrylate, and polyethylene glycol monomethacrylate; hydrophilic monomers such as acrylamide, methacrylamide, N-methylolacrylamide, N-methylolmethacrylamide, and diacetoneacrylamide; aromatic vinyl monomers such as styrene, α-methylstyrene, and halogenated styrene; vinyl esters such as vinyl acetate and vinyl propionate; unsaturated nitriles such as acrylonitrile; and ethylenically unsaturated alkyl carboxylates such as methyl acrylate, methyl methacrylate, ethyl acrylate, ethyl methacrylate, butyl acrylate, butyl methacrylate, 2-ethylhexyl acrylate, 2-ethylhexyl methacrylate, lauryl acrylate, lauryl methacrylate, stearyl acrylate, stearyl methacrylate, cyclohexyl acrylate, cyclohexyl methacrylate, isobornyl acrylate, and isobornyl methacrylate can be given. Other monomers (D) such as monomers having an unprotected carboxyl group such as acrylic acid, methacrylic acid, maleic acid, and itaconic acid, and monomers having a unprotected 2,3-dihydroxypropyl group such as 2,3-dihydroxypropyl (meth)acrylate may be used in a range not hindering the effect of the invention. The amount of the other monomers (D) used is a balance to the above monomers (A) to (C).

1.2.2. Polymerization Method

The organic polymer particles of this embodiment may be produced by a conventional method such as emulsion polymerization, soap-free polymerization, and suspension polymerization. Specifically, the organic polymer particles of this embodiment may be obtained by, for example, suspension polymerization of the above vinyl monomer or polymer bulk shattering.

For example, the organic polymer particles of this embodiment can be obtained by the two-step swelling polymerization method using seed particles (mother particles) described in JP-B-57-24369, the polymerization method described in J. Polym. Sci., Polymer Letter Ed., 21, 937 (1983), and the methods described in JP-A-61-215602, JP-A-61-215603, and JP-A-61-215604. Of these, the two-step swelling polymerization method using seed particles (mother particles) is preferable for reducing the coefficient of particle size variation. Polystyrene or a styrene-based copolymer can be used as seed particles (mother particles). The polymer part added by the two-step swelling polymerization method consists of a copolymer of the monomers (A) to (D).

As the emulsifier used when copolymerizing the monomers (A) to (D), anionic surfactants such as alkyl sulfate, alkylaryl sulfate, alkyl phosphate, and fatty acid salts; cationic surfactants such as alkyl amine salt and alkyl quaternary amine salt; nonionic surfactants such as polyoxyethylene alkyl ether, polyoxyethylene alkyl aryl ether, and block polyether; amphoteric surfactants such as carboxylic acid types (e.g. amino acids, betaine acids, and the like) and sulphonic acid types; reactive emulsifiers with commercial names such as Latemul S-180A, PD-104 (manufactured by KAO Corp.), Eleminol JS-2 (manufactured by Sanyo Chemical Industries, Ltd.), Aqualon HS-10, KH-10, RN-10, RN-20, RN-30, RN-50 (manufactured by Dai-ichi Kogyo Seiyaku Co., Ltd.), ADEKA REASOAP SE-10N, SR-10, NE-20, NE-30, NE40 (manufactured by ADEKA Corp.), and Antox MS-60 (manufactured by Nippon Nyukazai Co., Ltd.); and the like can be given. Reactive emulsifiers are particularly preferable due to excellent particle dispersability. Also, polymers having a hydrophilic group with a dispersion function may be used as the emulsifier. As examples of such polymers, styrene-maleic acid copolymer, styrene-acrylic acid copolymer, polyvinyl alcohol, polyalkylene glycol, sulfonated product of polyisoprene, sulfonated product of hydrogenated styrene-butadiene copolymer, sulfonated product of styrene-maleic acid copolymer, sulfonated product of styrene-acrylic acid copolymer, and the like can be given. These emulsifiers can be used either individually or in combination of two or more. Although there are no specific limitations to the amount of the emulsifier to be used, the amount is usually from 0.1 to 50 parts by weight, preferably from 0.2 to 20 parts by weight, and particularly preferably from 0.5 to 5 parts by weight for 100 parts by weight of the monomers (A) to (D). An amount less than 0.1 part by weight is not desirable due to insufficient emulsification and decline in stability during radical polymerization. On the other hand, an amount exceeding 50 parts by weight is not desirable due to a problem of foaming.

As the radical polymerization initiator used in the copolymerization of monomers (A) to (D), persulfates such as potassium persulfate, sodium persulfate, and ammonium persulfate; water-soluble initiators such as hydrogen peroxide, t-butyl hydroperoxide, t-butyl peroximaleate, succinic acid peroxide, and 2,2'-azobis[2-N-benzylamidino]propane hydrochloride; oil-soluble initiators such as benzoyl peroxide, cumene hydroperoxide, diisopropyl peroxydicarbonate, cumyl peroxyneodecanoate, cumyl peroxyoctanoate, and azobisisobutylonitrile; redox initiators using reducing agents such as acidic sodium sulfite, rongalite, and ascorbic acid; and the like can be given. As the radical polymerization initiator, an oil-soluble initiator which does not exhibit acidity or basicity in water is preferable.

1.3. Organic Polymer Particles Containing Magnetic Material and Process for Producing the Same The organic polymer particles of this embodiment may be organic polymer particles containing a magnetic material (fine magnetic material particles) (hereinafter referred to as "magnetic material-containing organic polymer particles"). Because the magnetic material-containing organic polymer particles can be separated using a magnet without using centrifugation, for example, a step for separating particles from samples to be inspected can be simplified or automated.

Although there are no limitations to the composition of the fine magnetic material particles of this embodiment as long as the material is magnetic, an iron oxide substance typified by ferrite of the formula $MFe_2O_4$ (M=Co, Ni, Mg, Cu, $Li_{0.5}Fe_{0.5}$, and the like), magnetite shown by the formula $Fe_3O_4$, and $\gamma Fe_2O_3$ can be given. Especially, $\gamma Fe_2O_3$ and $Fe_3O_4$ are preferable due to their high saturation magnetization and low residual magnetization.

As fine magnetic material particles having a low residual magnetization required in this embodiment, for example, fine particles of ferrite and/or magnetite having a particle size of about 5 to 20 nm can be suitably used.

In addition, fine magnetic material particles of which the surface is hydrophobized can also be used. The method for hydrophobizing the surface of the fine magnetic material particles is not specifically limited. For example, a method of bonding the fine magnetic material particles with a compound having a part having a very strong affinity with the fine magnetic material particles and a hydrophobic part in the molecule by causing them to come in contact with each other can be given. As examples of such a compound, a silane compound represented by a silane coupling agent and a surfactant represented by a long-chain fatty acid soap can be given.

The use of fine magnetic material particles with a hydrophobized surface has an advantage of easy formation of a coating layer on the outside of a later-described magnetic material layer. The magnetic material layer used herein refers to a layer formed by accumulating a number of fine magnetic material particles.

A hydrophobizing treatment using a silane compound produces fine magnetic material particles excelling in chemical resistance, particularly in alkali resistance, and can effectively inhibit peel-off of fine magnetic material particles due to fall-out of the hydrophobic area, a decrease in magnetic performance, and mingling of soils such as removed fine magnetic material particles and floating surfactants. In this embodiment, the surface is regarded to be completely hydrophobized, when the fine magnetic material particles of which the surface is hydrophobized can disperse in toluene, for example.

Magnetic material-containing organic polymer particles include (I) particles comprising a continuous phase of a non-magnetic material such as an organic polymer with fine magnetic material particles being dispersed therein, (II) particles comprising a core of a secondary aggregate of fine magnetic material particles and a shell of non-magnetic material such as an organic polymer, (III) particles comprising nuclear particles of a non-magnetic material such as an organic polymer, a secondary aggregate layer (a magnetic material layer) of fine magnetic material particles (superparamagnetic fine particles) provided on the surface of the particles, and an organic polymer layer (a polymer part) on the outer layer of the magnetic material layer, and the like. Of these, particles (III), which are the particles having an organic polymer layer on the outer layer of the nuclear particles containing a secondary aggregate layer of fine magnetic material particles ("the nuclear particles containing a secondary aggregate layer of fine magnetic material particles" are hereinafter referred to as "mother particles") are preferable. The organic polymer used for the magnetic material-containing organic polymer particles with various structures, specifically the polymer forming the outermost surface of the particles, excluding a core portion of core-shell type particles, must have a carboxyl group and a 2,3-dihydroxypropyl group. The interface between the nuclear particles and the outer layer (a magnetic material layer) and the interface between the magnetic material layer and its outer layer (an organic polymer layer) may be in a state in which the components of both layers are present together.

The most preferable magnetic material-containing organic polymer particles have a crosslinked polymer covering mother particles containing nuclear particles and a magnetic material layer of superparamagnetic fine particles formed on the surface of the nuclear particles. In this instance, the magnetic material-containing organic polymer particles comprise the mother particles as cores and the crosslinked polymer (polymer part) as shells. Here, the crosslinked polymer can be obtained by the above-mentioned production process. Specifically, the crosslinked polymer can be obtained by copolymerizing 5 to 40 parts by weight of the monomer (A), 40 to 95 parts by weight of the monomer (B) producing a 2,3-dihydroxypropyl group by hydrolysis, 0 to 30 parts by weight of the crosslinkable monomer (C), and 0 to 55 parts by weigh of other monomers (D) and hydrolyzing the resulting copolymer.

As the method for producing mother particles with a magnetic material layer of superparamagnetic fine particles on the surface of nuclear particles, a method of dry-blending non-magnetic organic polymer particles and superparamagnetic fine particles and complexing these particles by physically applying a strong external force can be given, for example. As examples of the method for physically applying a strong force, a method of using a mortar, an automatic mortar, or a ball mill, a blade-pressuring type powder compressing method, a method of utilizing a machanochemical effect such as a mechnofusion method, and a method of using an impact in a high-speed air stream such as a jet mill, a hybridizer, or the like can be given. In order to efficiently produce a firmly bound complex, a strong physical adsorption force is desirable. As a method for applying a strong physical adsorption force, stirring using a vessel equipped with a stirrer at a peripheral velocity of stirring blades of preferably 15 m/sec or more, more preferably 30 m/sec or more, and still more preferably from 40 to 50 m/sec can be given. If the peripheral velocity of stirring blades is slower than 15 m/sec, a sufficient amount of energy for causing superparamagnetic fine particles to be absorbed onto the surface of the non-magnetic organic polymer particles may not be obtained. Although there are no specific limitations to the upper limit of the peripheral velocity of stirring blades, the upper limit of the peripheral velocity is determined according to the apparatus to be used, energy efficiency, and the like. Fine particles of ferrite and/or magnetite with a particle diameter of about 5 to 20 nm, for example, can be preferably used as the superparamagnetic fine particles in this embodiment.

The polymer part (shell) can be formed by copolymerizing 5 to 40 parts by weight of monomer (A) producing a carboxyl group by hydrolysis, 40 to 95 parts by weight of monomer (B) producing a 2,3-dihydroxypropyl group by hydrolysis, 0 to 30 parts by weight of crosslinkable monomer (C), and 0 to 55 parts by weigh of other monomers (D) in the presence of the mother particles (core part). The components used are as described above. A more specific method of polymerization is disclosed in JP-A-2004-205481 and the like. The conditions for hydrolysis treatment after the polymerization are also the same as described above. Magnetic material-containing organic polymer particles are preferably hydrolyzed under weakly acidic to basic conditions because hydrolysis under strongly acidic conditions may dissolve the superparamagnetic fine particles.

In order to inhibit dissolution of the superparamagnetic fine particles on the mother particles, the magnetic material-containing organic polymer particles may be formed after forming a coating layer on the surface of mother particles comprising nuclear particles with a magnetic material layer of superparamagnetic fine particles formed on the surface using another monomer part comprising 0 to 30 parts by weight of crosslinkable monomer (C) and 70 to 100 parts by weight wt % of other monomers (D), by copolymerizing 5 to 40 parts by weight of monomer (A) producing a carboxyl group by hydrolysis, 40 to 95 parts by weight of monomer (B) producing a 2,3-dihydroxypropyl group by hydrolysis, 0 to 30 parts by weight of crosslinkable monomer (C), and 0 to 55 parts by weight of other monomers (D) using these mother particles having the coating layer as cores to obtain particles with polymer parts (shells) formed thereon, followed by hydrolysis of the resulting particles. In the case of hydrolyzing the magnetic material-containing organic polymer particles in which the superparamagnetic fine particles are covered with a coating layer in this manner, a broader hydrolysis conditions from a strongly acidic to strongly basic conditions can be selected.

It is desirable to remove residual hydrolysis catalysts from the dispersions of the organic polymer particles after hydrolysis and magnetic material-containing organic polymer particles by repeatedly washing these particles with water by a centrifugal separation method or a magnetic separation method.

1.4. Application

The organic polymer particles of this embodiment can be used as an affinity carrier such as particles for chemical compound-binding carrier in the biochemical field, particles for chemical-binding carrier for diagnostics, and the like, and particularly can exhibit remarkably high sensitivity and low noise as probe-bound particles for immunoassay bound with a primary probe such as an antigen or an antibody.

In the probe-bound particles of this embodiment, the substances to be inspected are biological-related substances and chemical compounds which are contained in immunoassay reagents and inspection samples. In the invention, the term "biological-related substance" refers to all substances relating to biological bodies. As examples of the biological-related substance, substances contained in biological bodies, substances derived from substances contained in biological bodies, and substances which can be used in biological bodies can be given. For example, the biological-related substances include, but are not limited to, proteins (e.g. enzymes, antibodies, aptamers, acceptors, etc.), peptides (e.g. glutathione, etc.), nucleic acids (e.g. DNA, RNA, etc.), carbohydrates, lipids, hormones (e.g., luteinizing hormones, human chorionic gonadotropins, thyroid stimulating hormones, insulin, glucagon, growth hormones, etc.), and other cells and substances (e.g., various blood-origin substances containing various blood cells such as platelets, erythrocytes, and leukocytes; various floating cells; and proteins and nucleic acids which are components of viruses, bacteria, fungi, protozoans, and parasites). As more specific examples of the proteins, proteins of biological origin, proteins used as a marker of various cancers such as a prostate gland unique marker and a bladder cancer marker, and the like can be given.

There are no specific limitations to the chemical substances to be detected. For example, environmental pollutants such as dioxins and medical supplies (for example, antibiotics, anticancers, antiepileptic drugs, etc.) can be given.

There are no specific limitations to the target biological substances to be detected. For example, various cancer cells, various floating cells, viruses (for example, hepatitis B virus, hepatitis C virus, simple herpes virus, HIV, German measles virus, influenza virus, etc.), bacteria (for example, *Neisseria gonorrhoeae*, MRSA, *Escherichia coli*, etc.), fungi (for example, *Candida, trichophytia bacillus, Cryptococcus, Aspergillus*, etc.), protozoan, parasites (for example, *toxoplasma*, malaria, etc.), and the like can be given.

According to the precursor of the probe-bound particles of the embodiment in which carboxyl groups are introduced on the surface of the particles, since the carboxyl groups are activated by known activators such as a water-soluble carbodiimide in actual use, a primary probe can be chemically bound onto the surface of the particles by mixing the primary probe and the particles.

After binding the primary probe onto the surface of the particles, an excess amount of the primary probe is washed out and unreacted activated carboxyl groups are deactivated as required. In addition, the primary probe bound onto the surface of the particles may be blocked by means of a conventional blocking operation or a blocking agent such as albumin may be used in the deactivation step. A conventional analytical procedure using the particles may be applied to the following steps.

Proteins (antigens or antibodies) or nucleic acids are used as a probe to be carried on the probe-bound particles of this embodiment. Of these, antigens and antibodies are preferable probes. In this case, there are no specific limitations to the antigens and antibodies inasmuch as the antigen or antibody reacts with components commonly contained in samples to be assayed. Examples include, but are not limited to, antigens or antibodies for coagulation-fibrinolysis-related inspections such as an anti-antiplasmin antibody for antiplasmin inspection, an anti-D dimer antibody for D dimer inspection, an anti-FDP antibody for FDP inspection, an anti-tPA antibody for tPA inspection, an antithrombin-antithrombin complex antibody for TAT inspection, an anti-FPA antibody for FPA inspection, and the like; antigens and antibodies for tumor-related inspections such as an anti-BFP antibody for BFP inspection, an anti-CEA antibody for CEA inspection, an anti-AFP antibody for AFP inspection, an anti-ferritin antibody for ferritin inspection, anti-CA19-9 antibody for CA19-9 inspection, and the like; antigens and antibodies for serum protein-related inspections such as anti-apolipoprotein antibody for apolipoprotein inspection, an anti-$\beta$2-microbloblin antibody for $\beta$2-microbloblin inspection, an anti-$\alpha$1-microglobulin antibody for $\alpha$1-microglobulin inspection, an anti-immunoglobulin antibody for immunoglobulin inspection, an anti-CRP antibody for CRP inspection, and the like; antigens and antibodies for endocrine function inspection such as an anti-HCG antibody for HCG inspection; antigens and antibodies for infection-related inspection such as anti-HBs antibody for HBs antigen inspection, an HBs antigen for HBs antibody inspection, an HCV antigen for HCV antibody inspection, an HIV-1 antigen for HIV-1 antibody inspection, an HIV-2 antigen for HIV-2 antibody inspection, an HTLV-1 antigen for HTLV-1 inspection, a *mycoplasma* antigen for mycoplasmatic disease inspection, a *toxoplasma* antigen for *toxoplasma* inspection, a streptolysin O antigen for anti-streptolysin O inspection, and the like; antigens and antibodies for autoimmune related inspections such as a DNA antigen for anti-DNA antibody inspection, a heat-denatured human IgG for RF inspection, and the like; and antigens and antibodies for analysis of drugs such as an anti-digoxin antibody for digoxin inspection, an anti-lidocaine antibody for lidocaine inspection, and the like. As the antibody, either polyclonal antibodies or monoclonal antibodies may be used.

The organic polymer particles of this embodiment can also be used as an affinity carrier for sensing proteins such as an enzyme and hormone, nucleic acids such as a DNA and RNA, lipids, and physiologically active sugar chain compounds on the surface of particles by a chemical bonding method.

In addition, the organic polymer particles of this embodiment can be used for selecting and purifying proteins and the like (target molecules) exhibiting specific interactions with a target chemical compound for analysis (ligand molecules) by immobilizing the ligand molecules by chemical bonding and analyzing and/or measuring the specific interactions using specific interactions with the proteins and the like.

The ligand molecules to be bound with the particles are not specifically limited insofar as such a ligand molecule has a functional group which can react with at least one of the carboxyl group or 2,3-dihydroxypropyl group possessed by the organic polymer particles of this embodiment. For example, nucleic acids, peptide nucleic acids, hormones, proteins with a molecular weight of 500 to 1,000,000, sugar chains, polysaccharides, cells, aptamers, viruses, enzymes, tag capturing chemicals for various affinities, coenzymes such as biotin, chemical compounds which have or may have a specific bioactivity can be used.

In addition to the above-mentioned applications, the organic polymer particles of this embodiment can be used in a wide variety of fields such as paints, papers, electronic materials, electrophotography, cosmetics, medical supplies, agricultural chemicals, foods, and catalysts.

2. Second Embodiment

2.1. Magnetic Particles for Diagnostics

The magnetic particles for diagnostics of one embodiment are organic polymer particles comprising fine magnetic material particles and a polymer part containing a hydrophilic polymer part and a crosslinked polymer part, a dry coating film obtained from a water dispersion thereof having a contact angle with water of 5° to 60°.

In a preferable inner structure of the magnetic particles for diagnostics of this embodiment, for example, the polymer part has a nuclear particle (polymer core part) and a coating layer (polymer coating layer), the fine magnetic material particles forms a magnetic material layer, the magnetic material layer is present on the outside of the nuclear particles, and the coating layer is formed on the outside of the magnetic material layer.

Each of the components of the magnetic particles for diagnostics of this embodiment is described below.

2.1.1. Fine Magnetic Material Particles

The fine magnetic material particles described in the first embodiment can be used as the fine magnetic material particles for this embodiment.

2.1.2. Polymer Part

The polymer part of the magnetic particles for diagnostics of this embodiment has a hydrophilic polymer part and a crosslinked polymer part. The polymer part can be obtained by polymerizing a raw material monomer (monomer part) containing a hydrophilic monomer and a crosslinkable monomer.

2.1.2-1. Hydrophilic Polymer Part

The hydrophilic polymer part is a component for forming the polymer part and has a function of ensuring that the dry coating film obtained from the water dispersion of the magnetic material particles for diagnostics of this embodiment has a low contact angle with water. The hydrophilic polymer part can be obtained from the hydrophilic monomer by polymerization of the monomer part.

The hydrophilic monomer may be a monomer that can be reduced from the molecular structure of the polymer which preferably has solubility in water at 25° C. of 10 g/100 cc or more.

The hydrophilic monomer is preferably hydrophilic while being non-crosslinkable. As examples of a non-crosslinkable hydrophilic monomer, a (meth)acrylate having a hydrophilic functional group such as a glycerol acrylate, glycerol methacrylate, 2-hydroxyethyl acrylate, 2-hydroxyethyl methacrylate, methoxyethyl acrylate, methoxyethyl methacrylate, polyethylene glycol monoacrylate, polyethylene glycol monomethacrylate, acrylic acid, methacrylic acid, acrylamide, methacrylamide, N-methylolacrylamide, N-methylolmethacrylamide, diacetoneacrylamide, allyl glycidyl ether, and the like can be given. The hydrophilic polymer part of the polymer part can be obtained by polymerizing these monomers as the monomer part as is.

In this embodiment, the hydrophilic monomers include monomers that can be polymerized to form the hydrophilic polymer part.

For example, when a monomer having a glycidyl group (for example, glycidyl acrylate, glycidyl methacrylate, and the like) is used, the glycidyl group is hydrolyzed in the polymerization of the monomer part to form the glycerol group (2,3-dihydroxypropyl group) in the aqueous dispersant of the magnetic particles for diagnostics of this embodiment. Specifically, a monomer having a glycidyl group can be polymerized to form a hydrophilic polymer part having a glycerol group (2,3-dihydroxypropyl group) which is a hydrophilic group including an alcoholic hydroxyl group. Therefore, the hydrophilic monomer of this embodiment includes a monomer having a glycidyl group.

In addition, when a vinyl ester (for example, vinyl acetate, vinyl propionate, and the like) is used as the monomer part, the ester site after polymerization can be intentionally hydrolyzed to form a hydrophilic polymer part. In this instance, the hydrophilic monomer includes a vinyl ester.

2.1.2-2. Crosslinked Polymer Part

The crosslinked polymer part is a component for forming the polymer part and has a function of adjusting the viscosity of the pellets so that the viscosity after magnetic separation may not become too low. The crosslinked polymer part can be obtained from a crosslinkable monomer by the polymerization of a monomer part.

The crosslinkable monomer is preferably a monomer having two or more vinyl groups in one molecule. The crosslinkable monomer may be either hydrophilic or non-hydrophilic.

As examples of the non-hydrophilic crosslinkable monomers, polyfunctional (meth)acrylates such as ethylene glycol diacrylate, ethylene glycol dimethacrylate, trimethylolpropane triacrylate, trimethylolpropane trimethacrylate, pentaerythritol triacrylate, pentaerythritol trimethacrylate, dipentaerythritol hexacrylate, dipentaerythritol hexamethacrylate; conjugated diolefins such as butadiene and isoprene; divinylbenzene, diallyl phthalate, allyl acrylate, allyl methacrylate, and the like can be given.

As examples of the hydrophilic crosslinkable monomers, polyethylene glycol diacrylate, polyethylene glycol dimethacrylate, poly(meth)acrylates of polyvinyl alcohol, and the like can be given. When the polymer part is formed using the hydrophilic crosslinkable monomer, the polymer part may have a hydrophilic crosslinked polymer part. Specifically, in this instance, the crosslinked polymer part is also the hydrophilic polymer part.

2.1.2-3. Other Monomers

The monomer part used to form the polymer part of the magnetic particles for diagnostics of this embodiment may include other monomers in addition to the hydrophilic monomer and the crosslinkable monomer. As examples of the other monomers, monomers that are non-hydrophilic while being non-crosslinkable can be given.

As examples of the non-crosslinkable non-hydrophilic monomer, aromatic vinyl monomers such as styrene, α-methylstyrene, and styrene halide; vinyl esters such as vinyl acetate and vinyl propionate (when used after polymerization without hydrolysis); unsaturated nitriles such as acrylonitrile; and ethylenically unsaturated alkyl carboxylates such as methyl acrylate, methyl methacrylate, ethyl acrylate, ethyl methacrylate, butyl acrylate, butyl methacrylate, 2-ethylhexyl acrylate, 2-ethylhexyl methacrylate, lauryl acrylate, lauryl methacrylate, stearyl acrylate, stearyl methacrylate, cyclohexyl acrylate, cyclohexyl methacrylate, isobornyl acrylate, and isobornyl methacrylate can be given.

2.1.2-4. Structure of Polymer Part

The polymer part of this embodiment may be either (i) a homopolymer of a hydrophilic and crosslinkable monomer or (ii) a copolymer of two or more monomers containing the above-described hydrophilic monomer and crosslinkable monomer as essential components. In the polymer part of the above case (i), since the hydrophilic polymer part is crosslinkable, the hydrophilic polymer part is also a crosslinkable polymer part. In the case (ii), the hydrophilic polymer part is obtained from the hydrophilic monomer by polymerization of the monomer part and the crosslinked polymer part can be obtained from the crosslinkable monomer by polymerization of the monomer part.

The polymer part of this embodiment may also be a blend polymer containing two or more types of at least one of the homopolymer of (i) and the copolymer of (ii), or a polymer part having a core-shell structure in which the homopolymer of (i) is the core (or the shell) and the copolymer of (ii) is the shell (or the core).

2.1.3. Water Dispersion

The magnetic particles for diagnostics of this embodiment can be used by being dispersed in a dispersion medium. As an example of the dispersion medium, an aqueous medium can be given. There are no specific limitations to the type of the aqueous medium. Water and water containing aqueous solvents can be given as examples. As examples of the aqueous solvent, alcohols such as ethanol, an alkylene glycol, a monoalkyl ether, and the like can be given.

In this embodiment, the term "water dispersion" refers to a dispersion using purified water as a dispersion medium. When a dispersion contains components other than water such as a surfactant, a water dispersion can be obtained by replacing the supernatant liquid several times with purified water.

2.1.4. Contact Angle of Dry Coating Film Obtained from a Water Dispersion with Water The contact angle of a dry coating film, which is made from a water dispersion of the magnetic particles for diagnostics of this embodiment, with water is from 5° to 60°, preferably from 10° to 50°, and most preferably from 10° to 40°. If the contact angle is less than 5°, the viscosity of pellets after magnetic separation is too low; if more than 60°, non-specific adsorption of proteins and nucleic acids increases.

In the invention, "a dry coating film made from a water dispersion" (hereinafter referred to also as "dry coating film") refers to a coating film obtained by preparing a water dispersion by dispersing 50 mg of the magnetic particles in 0.2 ml of purified water, applying this water dispersion to a flat and smooth substrate such as a glass slide using an applicator or the like, and drying the coating at a humidity of 40% and a temperature of 25° C. for 24 hours.

The contact angle of the dry coating film with water can be determined by dripping about 1 µl of water on the dry coating film, immediately acquiring the image data from the horizontal direction using a camera, and measuring the angle between the outline of the water drop and the horizon of the coating film, assuming that the outline of the water drop is a part of a circle's perimeter.

The contact angle of water with the dry coating film obtained from the water dispersion can be controlled by adjusting the ratio of the hydrophilic monomer and non-hydrophilic polymer part (e.g. non-hydrophilic crosslinkable monomer) used for producing the magnetic particles for diagnostics of the this embodiment. Although it depends on the internal structure of the magnetic particles for diagnostics of this embodiment, the contact angle can be decreased (increased) by, for example, increasing (decreasing) the ratio of the hydrophilic monomer used for forming the polymer part (coating layer) at least on the outermost surface of the magnetic particles. In addition, use of a non-hydrophilic crosslinkable monomer in forming a polymer part can prevent the viscosity of the pellets after magnetic separation from becoming too low.

2.1.5. Internal Structure of Magnetic Particles

In the magnetic particles for diagnostics of this embodiment, the fine magnetic material particles and the polymer part are present for example, in a manner in which the fine magnetic material particles are dispersed homogeneously in a continuous phase of the polymer part, or in a manner in which the fine magnetic material particles and the polymer part are unevenly distributed forming a core-shell structure.

In the case in which the magnetic particles for diagnostics of this embodiment have a core-shell structure, the polymer part is included in either the core or the shell which covers the core, or in both the core and the shell. In this instance, the fine magnetic material particles may be present in either the core or the shell, or both.

A preferable internal structure of the magnetic particles of this embodiment is a structure containing nuclear particles (a polymer core part), magnetic material layer (a layer of fine magnetic material particles) existing on the outside of the nuclear particles, and a coating layer (a polymer coat layer) existing on the outside of the magnetic material layer. The method for producing such magnetic particles is disclosed in JP-A-2004-205481. The interface between the nuclear particles and the outer layer (the magnetic material layer) and the interface between the magnetic material layer and its outer layer (the coating layer) may be in a state in which the components of both layers are present together. In the magnetic particles for diagnostics of this embodiment, it is desirable that the coating layer contain the hydrophilic polymer part and the hydrophilic polymer part has an alcoholic hydroxyl group. Specifically, it is desirable that the alcoholic hydroxyl group be present at least on the surface of the magnetic particles of this embodiment.

In this structure, monomers for forming the nuclear particles do not necessarily have to contain a hydrophilic monomer and a crosslinkable monomer. As a preferable combination of monomers forming the nuclear particles, a combination of non-hydrophilic non-crosslinkable monomers, as main monomers, and a small amount of hydrophilic monomers and/or crosslinkable monomers can be given.

As the method for forming a magnetic material layer on the outside of the nuclear particles, a method for forming a magnetic-material layer on the surface of the nuclear particles by mixing the nuclear particles with the fine magnetic material particles to cause the fine magnetic material particles to be adsorbed on the surface of the nuclear particles by physical adsorption can be given, for example. Here, "physical adsorption" refers to adsorption not involving a chemical reaction. As the principle of "physical adsorption", hydrophobic/hydrophobic adsorption, molten bond or adsorption, fusion bond or adsorption, hydrogen bond, Van-der-Waals force bond, and the like can be given, for example. As the method for hydrophobic/hydrophobic adsorption, for example, a method of selecting nuclear particles and fine magnetic material particles of both of which the surface is hydrophobic or hydrophobized and dry-blending these nuclear particles and fine magnetic material particles, and a method of sufficiently dispersing the nuclear particles and fine magnetic material particles in a solvent (e.g. toluene or hexane) with good dispersibility without damaging both of the particles, followed by vaporization of the solvent while mixing can be given.

Alternatively, fine magnetic material particles can be caused to attach to the surface of the nuclear particles by, for example, physically applying a strong force from the outside, thereby forming a complex of the nuclear particles and the fine magnetic material particles. As a method for physically applying a strong force from the outside, the method previously described in the first embodiment can be given, for example. Superparamagnetic fine particles are preferable for use as the fine magnetic material particles in this embodiment. As the superparamagnetic fine particles, fine particles of ferrite and/or magnetite with a particle diameter of 5 to 20 nm, for example, can be preferably used.

Next, as the method for forming a coating layer on the outside of the nuclear particles, a method of forming a magnetic material layer on the surface of the nuclear particles and reacting them with monomers in a dispersing medium can be given. As the monomers for forming the coating layer, the above-mentioned monomers can be used. A preferable combination is a combination of a hydrophilic monomer and crosslinkable monomer as main components. The coating layer may consist of multi-polymer components of two or more layers.

2.1.6. Most Preferable Constitution (1)

A first most preferable constitution of the magnetic particles for diagnostics of this embodiment is "magnetic particles containing nuclear particles, a magnetic material layer existing on the outside of the nuclear particles, and a coating layer existing on the outside of the magnetic material layer, in which the hydrophilic polymer part has an alcoholic hydroxyl group, the coating layer contains this hydrophilic polymer part, and a dry coating film obtained from a water dispersion thereof has a contact angle with water of 10° to 30°".

In order to form the hydrophilic polymer part having an alcoholic hydroxyl group, it is preferable to use a hydrophilic monomer which can form the hydrophilic polymer part containing an alcoholic hydroxyl group after polymerization. As examples of such a hydrophilic monomer, glycidyl acrylate, glycidyl methacrylate, glycerol acrylate, glycerol methacrylate, allyl glycidyl ether, and (meth)acrylate of polyvinyl alcohol can be given.

The above constitution ensures the magnetic particles for diagnostics of this embodiment to exhibit extremely low non-specific adsorption of proteins and nucleic acids and a high S/N ratio when using the particles in the ELISA method.

2.1.6. Most Preferable Constitution (2)

A second most preferable constitution of the magnetic particles for diagnostics of this embodiment is "magnetic particles containing nuclear particles, a magnetic material layer existing on the outside of the nuclear particles, and a coating layer existing on the outside of the magnetic material layer, in which the hydrophilic polymer part has a carboxyl group, the coating layer contains this hydrophilic polymer part, and a dry coating film obtained from a water dispersion thereof has a contact angle with water of 20° to 40°".

In order to form the hydrophilic polymer part having a carboxyl group, it is preferable to use a hydrophilic monomer which can form the hydrophilic polymer part containing a carboxyl group after polymerization. As examples of such a hydrophilic monomer, acrylic acid, methacrylic acid, itaconic acid, fumaric acid, crotonic acid, and the like can be given.

The above constitution ensures the magnetic particles for diagnostics of this embodiment to bind particularly with a large amount of proteins such as an antibody and avidin. The particles can bind with a larger amount of proteins when the particle surface is porous.

The carboxylic acid-reduced surface charge amount of the magnetic particles is preferably from 50 to 400 µmol/g, and more preferably from 70 to 300 µmol/g.

2.1.8. Use

As the use of the magnetic particles for diagnostics of this embodiment, those mentioned in connection with the organic polymer particles of the first embodiment can be given. A biochemical carrier is a main use, in which the particles are used as medical diagnostics, particularly as particles for automatic analyzers. The magnetic particles for diagnostics of this embodiment can be used as biotin-binding particles by immobilizing a substance having a site that can bind with biotins (later-described biotin and biotin derivatives) on the surface thereof. As the substance having a biotin-binding site, avidin and avidin derivatives such as streptavidin can be given.

When the magnetic particles for diagnostics of this embodiment are used as biochemical carrier particles, the following manners of use can be given, for example. A use of binding the magnetic particles for diagnostics of this embodiment with an antibody and causing the antibody to bind with an antigen such as viruses, bacteria, cells, hormones, and chemical compounds such as dioxins, thereby collecting and concentrating the antigens. A use of binding the magnetic particles for diagnostics of this embodiment with a nucleic acid analog such as a DNA and causing a nucleic acid to bind with the nucleic acid analog by hybridization to collect or detect the nucleic acid or causing a protein or a chemical compound such as coloring matter that can bind with a nucleic acid to bind with the nucleic acid analog to collect or detect such a protein or chemical compound. A use of binding the magnetic particles for diagnostics of this embodiment with avidins (or biotins) and causing a molecule having biotins (or avidins) to bind with the avidins (or biotins) to collect and detect the biotins (or avidins). A use of binding the magnetic particles for diagnostics of this embodiment with an antibody or an antigen to use the particles as a carrier for enzyme immunoassay using a colorimetric method or chemoluminescence. The above uses can be applied to particles of other embodiments in which such particles of other embodiments are used as biochemical carrier particles.

If the magnetic particles for diagnostics of this embodiment are used, any diagnostic items using a 96-well plate or the like as a carrier can generally be replaced with an automatic analyzer using magnetism. As the target substances of diagnosis, those previously described in the first embodiment can be given, for example.

3. Third Embodiment 3.1. Carboxyl Group-Containing Particles and Process for Producing Same The process for producing the carboxyl group-containing particles of one embodiment of the invention comprises a step of producing an ester bond by reacting a hydroxyl group in organic polymer particles having the hydroxyl group with a carboxylic anhydride. Specifically, the carboxyl group-containing particles obtained by the above process contains a functional group possessing an ester bond.

3.1.1. Process for Producing Carboxyl Group-Containing Particles 3.1.1-1. Hydroxyl Group-Containing Organic Polymer Particles The hydroxyl group contained by the organic polymer particles is preferably an alcoholic hydroxyl group, with a polyvalent alcohol containing an α,β-diol being particularly preferable, and a 2,3-dihydroxypropyl group being the most preferable. The organic polymer particles preferably contain a hydroxyl group at least on the surface.

The following (i) to (iv) can be given as examples of the hydroxyl group-containing organic polymer particles.

(i) 2,3-dihydroxypropyl group-containing organic polymer particles

The 2,3-dihydroxypropyl group (i) has two hydroxyl groups in one functional group. The organic polymer particles having a 2,3-dihydroxypropyl group can be prepared, for example, from a monomer (A) having a 2,3-dihydroxypropyl group (hereinafter referred to simply as "monomer (A)") by homopolymerization of monomer (A) or copolymerization with other monomers, or from a monomer (B) producing a 2,3-dihydroxypropyl group by hydrolysis (hereinafter referred to simply as "monomer (B)") by homopolymerization of monomer (B) or copolymerization with other monomers, followed by hydrolysis of the resulting organic polymer. Alternatively, it is possible to produce the organic polymer particles using both the monomer (A) and the monomer (B). The use of monomer (B) is preferred due to capability of introducing a larger amount of hydroxyl groups, which results in a low noise, and due to stable polymerization.

As examples of the monomer (A) having a 2,3-dihydroxypropyl group, radically polymerizable monomers such as glycerol (meth)acrylate and allyl glycerol ether can be given.

As the monomer (B) producing a 2,3-dihydroxypropyl group by hydrolysis, a monomer having a functional group in which the hydroxyl group is protected by a known protecting group, for example, (B-1) a monomer having a 2,3-epoxypropyl group, (B-2) a monomer obtained by acetalating a 2,3-dihydroxypropyl group, and (B-3) a monomer obtained by silylating a 2,3-dihydroxypropyl group can be given. As specific examples of the (B-1) monomer having a 2,3-epoxypropyl group, glycidyl (meth)acrylate, allyl glycidyl ether, and the like can be given. As specific examples of the (B-2) monomer obtained by acetalating a 2,3-dihydroxypropyl group, 1,3-dioxolan-2-on-4-ylmethyl (meth)acrylate, 1,3-dioxolane-2,2-dimethyl-4-ylmethyl (meth)acrylate, and the like can be given. As specific examples of the (B-3) monomer obtained by silylating a 2,3-dihydroxypropyl group, di(t-butyl)silylated compound of 2,3-dihydroxypropyl (meth)acrylate, di(trimethylsilyl)ated compound of 2,3-dihydroxypropyl (meth)acrylate, and the like can be given.

Although the conditions for hydrolyzing the functional group of the monomer (B) varies according to the type of the monomer (B), particles dispersed in water are usually stirred from several hours to several tens of hours while heating and using an acid, a base, or a fluoride salt as a catalyst to effect hydrolysis. In the hydrolysis of the functional group of the monomer (B), not all of the functional groups in the monomer (B) need to be hydrolyzed as long as storage stability and the like are not hindered. Although the hydrolysis of the functional group of the monomer (B) is usually conducted after polymerization of the monomer part, a portion of the functional group may be hydrolyzed during polymerization.

The monomer (A) and/or monomer (B) are preferably copolymerized with the crosslinkable monomer (C). The crosslinkable monomer (C) (hereinafter also referred to as "monomer (C)") is a monomer which can be copolymerized with the other monomers used and possesses two or more radically polymerizable unsaturated bonds in the molecule.

As examples of the crosslinkable monomer (C), polyfunctional (meth)acrylates such as ethylene glycol diacrylate, ethylene glycol dimethacrylate, trimethylolpropane triacrylate, trimethylolpropane trimethacrylate, pentaerythritol triacrylate, pentaerythritol trimethacrylate, dipentaerythritol hexacrylate, dipentaerythritol hexamethacrylate; conjugated diolefins such as butadiene and isoprene; divinylbenzene, diallyl phthalate, allyl acrylate, allyl methacrylate, and the like can be given.

As further examples of the crosslinkable monomer (C), hydrophilic monomers such as polyethylene glycol diacrylate, polyethylene glycol dimethacrylate, poly(meth)acrylates of polyvinyl alcohol, and the like can be given.

The amount of the crosslinkable monomer (C) is preferably from 0 to 30 wt % and particularly preferably from 5 to 20 wt % for 100 wt % of the copolymer. If the amount of the monomer (C) exceeds 30 wt %, the particles become porous, possibly causing non-specific adsorption to increase.

The monomer (A) and monomer (B) may be further copolymerized with other monomers (D). As examples of the other monomers (D), (meth)acrylates having a hydrophilic functional group such as 2-hydroxyethyl acrylate, 2-hydroxyethyl methacrylate, methoxyethyl acrylate, methoxyethyl methacrylate, polyethylene glycol monoacrylate, and polyethylene glycol monomethacrylate; hydrophilic monomers such as acrylamide, methacrylamide, N-methylolacrylamide, N-methylolmethacrylamide, and diacetoneacrylamide; aromatic vinyl monomers such as styrene, α-methylstyrene, and halogenated styrene; vinyl esters such as vinyl acetate and vinyl propionate; unsaturated nitriles such as acrylonitrile; and ethylenically unsaturated alkyl carboxylates such as methyl acrylate, methyl methacrylate, ethyl acrylate, ethyl methacrylate, butyl acrylate, butyl methacrylate, 2-ethylhexyl acrylate, 2-ethylhexyl methacrylate, lauryl acrylate, lauryl methacrylate, stearyl acrylate, stearyl methacrylate, cyclohexyl acrylate, cyclohexyl methacrylate, isobornyl acrylate, and isobornyl methacrylate can be given. Although other monomers (D) such as monomers having a carboxyl group such as acrylic acid, methacrylic acid, maleic acid, and itaconic acid may be used in a range not hindering the effect of the invention, it is preferable not to use monomers having a carboxyl group.

The most preferable combination of monomers is 80 to 95 parts of monomer (B) and 5 to 20 parts of monomer (C).

The organic polymer particles having a hydroxyl group obtained by polymerizing the above-described monomers can be produced by a conventional polymerization method such as emulsion polymerization, soap-free polymerization, and suspension polymerization. More specifically, the organic polymer particles can be obtained by the two-step swelling polymerization method using seed particles (mother particles) described in JP-B-57-24369, the polymerization method described in J. Polym. Sci., Polymer Letter Ed., 21, 937 (1983), and the methods described in JP-A-61-215602, JP-A-61-215603, and JP-A-61-215604. Of these methods, the two-step swelling polymerization method using seed particles (mother particles) is preferable for reducing the coefficient of particle size variation. Polystyrene or a styrene-based copolymer can be preferably used as seed particles (mother particles). The polymer part added by the two-step swelling polymerization method is a copolymer of the above monomers. In these polymerization methods, a known emulsifying agent, dispersant, initiator, and the like may be used.

Although radically polymerized polymer particles have been described as the organic polymer particles having a 2,3-dihydroxypropyl group, as examples of polymer particles having a 2,3-dihydroxypropyl group obtained by condensation polymerization, polyurethane particles, polyamide particles, polyester particles, and the like with the terminals being blocked by glycerol and the like can be given.

(ii) As the organic polymer particles having a polyhydric alcohol containing an α,β-diol other than (i), polyurethane particles, polyamide particles, polyester particles, and the like of which the terminals are blocked with a sugar or a reducing sugar; condensed polymer particles of which the terminals are blocked with a sugar or a reducing sugar; crystalline polysaccharides such as chitin, chitosan, starch, and cellulose; crosslinked particles of naturally-occurring or synthesized polysaccharide such as crosslinked dextrin, crosslinked cyclodextrin, and crosslinked pullulan, and the like can be given.

(iii) As organic polymer particles containing an alcoholic hydroxyl group other than the polymer particles (i) and (ii), (co)polymer particles of monomers containing a hydroxyalkyl group such as a hydroxylethyl (meth)acrylate and a hydroxylbutyl (meth)acrylate; partial hydrolyzates of polyvinyl acetate particles; crosslinked polyvinyl alcohol particles; and the like can be given.

(iv) As organic polymer particles containing a hydroxyl group other than the polymer particles (i) to (iii) above, silanol-modified organic polymer particles; complex polymer particles of a metal oxide such as silica, alumina, titania, or the like and an organic polymer particles; polysilsesquioxane particles; and the like can be given.

In the organic polymer particles having a hydroxyl group used in the process for producing the carboxyl group-containing particles of this embodiment, the hydroxyl group is not only a functional group that can produce an ester bond by reacting with carboxylic anhydride, but also a factor exhibiting low non-specific adsorption and high sensitivity. The amount of the hydroxyl group per the amount of solid components in the organic polymer particles having a hydroxyl group is preferably 10 µmol/g or more, more preferably 50 µmol/g or more, and most preferably 100 µmol/g or more. If the amount of the hydroxyl group is less than 10 µmol/g, non-specific adsorption may increase.

3.1.1-2. Carboxylic Anhydride and Ester Bond Thereof.

The carboxylic anhydride usable in the process for producing the carboxyl group-containing particles of this embodiment is preferably a polyvalent carboxylic anhydride, as specific examples, aliphatic dicarboxylic anhydrides such as itaconic anhydride, succinic anhydride, citraconic anhydride, dodecenylsuccinic anhydride, tricarbanylic anhydride, glutaric anhydride, maleic anhydride, hexahydrophthalic anhydride, methyltetrahydrophthalic anhydride, and himic anhydride; alicyclic polyvalent carboxylic dianhydrides such as 1,2,3,4-butanetetracarboxylic dianhydride and cyclopentanetetracarboxylic dianhydride; aromatic polyvalent carboxylic anhydrides such as phthalic anhydride, pyromellitic anhydride, trimellitic anhydride, and benzophenonetetracarboxylic anhydride; ester group-containing acid anhydrides such as ethylene glycol bis(anhydrous trimellitate) and glycerol tris (anhydrous trimellitate); and the like can be given. Of these, 1,2-dicarboxylic anhydride such as succinic anhydride, maleic anhydride, and phthalic anhydride is particularly preferable.

As an example of a specific method for producing an ester bond by reacting a hydroxyl group in the hydroxyl group-containing organic polymer particles and a carboxylic anhydride, a method of dispersing dry powder of the hydroxyl group-containing organic polymer particles in an organic solvent in which the carboxylic anhydride is dissolved and stirring the mixture at room temperature to 80° C. for 1 to 24 hours can be given. Examples of the organic solvent used here include, but are not limited to, pyridine, DMF, acetone, methyl ethyl ketone, tetrahydrofuran, and the like. As the catalyst, sulfuric acid, p-toluenesulfonic acid, zinc chloride, sodium acetate, pyridine, 4-dimethylaminopyridine, 4-pyrrolidinopyrridine, and triethylamine can be used. Of these organic solvents and catalysts, pyridine is suitable as an organic solvent and a catalyst.

It is not necessary that all of the hydroxyl groups on the above-mentioned organic polymer particles are esterified by reacting with a carboxylic anhydride, but it is desirable that some hydroxyl groups remain as is without being esterified.

3.1.2. Carboxyl Group-Containing Particles

The number average particle diameter (hereinafter referred to simply as "particle diameter") of the carboxyl group-containing particles of this embodiment is preferably from 0.1 to 15 µm, more preferably from 0.3 to 10 µm, and most preferably from 1 to 10 µm. The particle diameter can be determined by the laser diffraction-scattering method. If the particle diameter is less than 0.1 µm, it takes a long time for separation using centrifugation and the like, resulting in insufficient separation of particles from a washing solvent such as water. This makes it difficult to sufficiently remove molecules other than target molecules (e.g. biological-related substances such as proteins and nucleic acids), giving rise to possible inadequate purification. On the other hand, if the particle diameter is more than 15 µm, the sensitivity may be impaired as a result of a decrease in the amount of captured physiologically active substances due to small specific surface area.

The carboxyl group-containing particles of this embodiment have a carboxyl group. In producing the carboxyl group-containing particles of this embodiment, an ester bond and a carboxyl group can be produced by using a polyvalent carboxylic anhydride as the carboxylic anhydride and reacting the polyvalent carboxylic anhydride with the hydroxyl group in hydroxyl group-containing organic polymer particles. For example, particles having a functional group containing an ester bond and a carboxyl group can be produced by reacting a hydroxyl group originating from a 2,3-dihydroxypropyl group in organic polymer particles having the 2,3-dihydroxypropyl group with a polyvalent carboxylic anhydride.

In the carboxyl group-containing particles of this embodiment, the carboxyl group is not only a functional group that can bond to proteins, but also a factor of exhibiting dispersibility of the particles. The amount of the carboxyl group per the amount of solid components in the particles is preferably 2 µmol/g or more, more preferably 5 µmol/g or more, and most preferably from 10 to 100 µmol/g. If the amount of the carboxyl group is less than 2 µmol/g, the amount of signals may decrease.

The contact angle of a dry coating film, which is made from a water dispersion of the carboxyl group-containing particles of this embodiment, and water is preferably 60° or less, more preferably 50° or less, and most preferably from 10° to 40°. The dry coating film made from the water dispersion can be obtained by preparing a water dispersion by dispersing 50 mg of the particles in 0.2 ml of purified water, applying this water dispersion to a flat and smooth substrate such as a glass slide using an applicator or the like, and drying the coating at a humidity of 40% and a temperature of 25° C. for 24 hours. The contact angle of the dry coating film with water can be determined by dripping about 1 µl of water on the dry coating film, immediately acquiring the image data from the horizontal direction using a camera, and measuring the angle between the outline of the water drop and the horizon of the coating film, assuming that the outline of the water drop is a part of a circle's perimeter. Low non-specific adsorption and high sensitivity can be ensured at the same time by having the contact angle of a dry coating film made from a water dispersion of the carboxyl group-containing particles of this embodiment with water in the above ranges.

The carboxyl group-containing particles of this embodiment are usually used by dispersing in an appropriate dispersion medium. A dispersion medium not dissolving the organic polymer particles or not swelling the organic polymer particles are preferably used as the dispersion medium. An aqueous medium can be given as a preferable dispersion medium. The aqueous medium here refers to water or a mixture of water and an organic solvent miscible with water (e.g. alcohols, alkylene glycol derivatives, etc.).

The carboxyl group-containing particles of this embodiment not only can chemically bond to biological-related substances, including proteins such as an antibody or an antigen, by utilizing the carboxyl group, but also exhibits only small non-specific adsorption of proteins, nucleic acids, and the like of biological origin.

3.1.3. Process for Producing Carboxyl Group-Containing Particles Containing Magnetic Material The carboxyl group-containing particles of this embodiment may contain a magnetic material. The carboxyl group-containing particles containing magnetic material are hereinafter referred to also as "magnetic material-containing carboxyl group-containing particles". The fine magnetic material particles described in the first embodiment can be used as the magnetic material here.

Because the magnetic material-containing carboxyl group-containing particles can be separated using a magnet without using centrifugation, for example, a step for separating particles from samples to be inspected can be simplified or automated.

Magnetic material-containing carboxyl group-containing particles include (I) particles comprising a continuous phase of a non-magnetic material such as an organic polymer with fine magnetic material particles being dispersed therein, (II) particles comprising a core of a secondary aggregate of fine magnetic material particles and a shell of non-magnetic material such as an organic polymer, (III) particles comprising mother particles, which comprises nuclear particles of a non-magnetic material such as an organic polymer and a secondary aggregate layer (a magnetic material layer) of fine magnetic material particles provided on the surface of the nuclear particles, as a core, and a polymer part (an organic polymer layer) on the outermost layer of the mother particles, as a shell, and the like. Of these, (III) particles consisting of a core of the mother particles containing a secondary aggregate layer of fine magnetic material particles and a shell of a polymer part are preferable. The interface between the nuclear particles and the outer layer (a magnetic material layer) and the interface between the magnetic material layer and its outer layer (a polymer layer) may be in a state in which the components of both layers are present together.

The organic polymer used for the magnetic material-containing carboxyl group-containing particles having the structures (I) to (III) above must have hydroxyl groups on the outermost surface, excluding core sections of the core-shell type particles.

The most preferable magnetic material-containing carboxyl group-containing particles comprise mother particles containing nuclear particles and a magnetic material layer of superparamagnetic fine particles formed on the surface of the nuclear particles and a polymer part of crosslinked polymer covering the mother particles. In this instance, the magnetic material-containing carboxyl group-containing particles comprise the mother particles as cores and the crosslinked polymer as shells. More specifically, an appropriate crosslinked polymer can be obtained by copolymerizing 40 to 95 parts by weight of the monomer (B), 5 to 30 parts by weight of the crosslinkable monomer (C), and 0 to 55 parts by weigh of other monomers (D) and hydrolyzing the resulting copolymer.

As the method for preparing mother particles having nuclear particles having a magnetic material layer of superparamagnetic fine particles formed on the surface in the process for producing the particles of the above structure (III), the method described in the first embodiment can be given, for example. Fine particles of ferrite and/or magnetite with a particle diameter of 5 to 20 nm, for example, can be preferably used as the superparamagnetic fine particles in this embodiment.

The polymer part (shell) can be formed by copolymerizing 40 to 95 parts by weight of the monomer (B), 5 to 30 parts by weight of the crosslinkable monomer (C), and 0 to 55 parts by weigh of other monomers (D) and hydrolyzing the resulting polymer. The monomer components used are as described above. A more specific method of polymerization is disclosed in JP-A-2004-205481 and the like. The conditions for hydrolysis treatment after the polymerization are also the same as described above.

In order to inhibit dissolution of the superparamagnetic fine particles on the mother particles, the magnetic material-containing carboxyl group-containing particles may be formed after forming a coating layer on the surface of mother particles comprising nuclear particles with superparamagnetic fine particles formed on the surface by polymerizing another monomer part comprising 0 to 30 parts by weight of crosslinkable monomer (C) and 70 to 100 parts by weight of other monomers (D), by copolymerizing 40 to 95 parts by weight of monomer (B), 5 to 30 parts by weight of crosslinkable monomer (C), and 0 to 55 parts by weight of other monomers (D) using these mother particles having the coating layer as cores to obtain particles with polymer part (shells), followed by hydrolysis of the resulting particles. In the case of hydrolyzing the magnetic material-containing carboxyl group-containing particles in which the superparamagnetic fine particles are covered with a coating layer in this manner, a broader hydrolysis conditions from a strongly acidic to strongly basic conditions can be selected.

It is desirable to remove residual hydrolysis catalysts from the dispersions of the low non-specific adsorption particles and the magnetic material-containing carboxyl group-containing particles after hydrolysis by repeatedly washing these particles with water by a centrifugal separation method or a magnetic separation method.

3.2. Use

The carboxyl group-containing particles of this embodiment can be used in a wide variety of fields such as biochemistry field, paints, papers, electronic photographs, cosmetics, medical supplies, agricultural chemicals, foods, and catalysts.

More specifically, the carboxyl group-containing particles of this embodiment are useful as a carrier for diagnostics, a carrier for bacteria separation, a carrier for cell separation, a carrier for separation and purification of nucleic acid, a carrier for separation and purification of proteins, a carrier for immobilizing enzyme, a drug delivery carrier, and the like. Above all, the particles can be used as an affinity carrier such as particles for chemical compound-binding carrier in the biochemical field, particles for chemical-binding carrier for diagnostics, and the like, particularly can exhibit remarkably high sensitivity and low noise as probe-bound particles for immunoassay bound with a protein such as an antigen or an antibody (particles for protein-binding).

In the probe-bound particles of this embodiment, the substances to be inspected include biological-related substances, chemical compounds, and living organism which are contained in immunoassay reagents and inspection samples.

As the target biological-related substances, chemical compounds for inspection, those previously described in the first embodiment can be given, for example.

Since the carboxyl groups are introduced on the surface of the carboxyl group-containing particles of this embodiment, a protein can be chemically bound on the surface of the particles by activating the carboxyl group site by a known activator such as a water-soluble carbodiimide and mixing the particle with the protein in actual use.

After binding the protein onto the surface of the particles, an excess amount of the protein is washed out and unreacted activated carboxyl sites are deactivated as required. In addition, after the protein was adsorbed onto the surface of the particles, the surface may be blocked by means of a conventional blocking operation or a blocking agent such as albumin may be used in the deactivation step. A conventional analytical procedure using particles may be applied to the following steps.

The protein to be carried on the carboxyl group-containing particles for protein binding of this embodiment is preferably an antigen or an antibody. In this case, there are no specific limitations to the antigens and antibodies inasmuch as the antigen or antibody reacts with components commonly contained in samples to be assayed. Examples described in the first embodiment can be given.

The carboxyl group-containing particles of this embodiment can be preferably used for a biochip using particles, for example, the biochip disclosed in JP-A-2005-148048.

The field of application of the carboxyl group-containing particles of this embodiment is not limited to carrier for biochemical substances, but includes the above-mentioned various fields.

4. Fourth Embodiment

4.1. Organic Polymer Particles and Process for Producing Same

4.1.1. Constitution of Organic Polymer Particles

The organic polymer particles of one embodiment of the invention have a hydroxyl group originating from a 2,3-dihydroxypropyl group and a polyoxyethylene group. The organic polymer particles of this embodiment may have a polyoxyethylene group and a 2,3-dihydroxypropyl group, for example, at least on the surface of the particles.

Either the entirety of the organic polymer particles of this embodiment may consist of a polymer part or the organic polymer particles may have a core-shell structure, with the shell being formed of a polymer part. Specifically, the polymer part may contain a polymer having a hydroxyl group originating from a 2,3-dihydroxypropyl group and a polyoxyethylene group.

In the organic polymer particles of this embodiment, the polyoxyethylene group $[H-(O-CH_2-CH_2-)_n-O-]$ (wherein n is an integer of 2 or more) is a factor for exhibiting good dispersibility and low noise.

In the organic polymer particles of this embodiment, the amount of the polyoxyethylene group is preferably from 0.1 to 10 parts by weight and particularly preferably from 0.5 to 3 parts by weight for 100 parts by weight of the polymer component on the surface of the organic polymer particles. If the polyoxyethylene group is used in an amount less than 0.1 part by weight, dispersibility may become inferior; if the amount exceeds 10 parts by weight, the signals may degrade.

The amount of the polyoxyethylene group may be adjusted according to the types and amounts of the later-mentioned monomer (A), reactive emulsifier (R), and modifier (M). The number of the oxyethylene units in the polyoxyethylene group (represented by n in the formula $[H-(O-CH_2-CH_2-)_n-O-]$) is preferably from 2 to 150. If n is less than 2, dispersibility may be poor, and if more than 150, sensitivity may be poor.

Although one end of the polyoxyethylene group (the end not attached to the organic polymer particles) is usually a hydroxyl group, the end may be substituted with a sulfonic acid (sulfonate) group, phosphoric acid (phosphate) group, carboxylic acid (carboxylate) group, methyl group, or the like. When the end of the polyoxyethylene group is substituted with an anionic functional group, dispersibility is even more excellent. On the other hand, in order to exhibit low noise, the end of the polyoxyethylene group is preferably not substituted with these functional groups.

In the organic polymer particles of this embodiment, the 2,3-dihydroxypropyl group is a factor for exhibiting high sensitivity and low noise. The amount of the 2,3-dihydroxypropyl group per the amount of solid components in the organic polymer particles is preferably 10 μmol/g or more, more preferably 50 μmol/g or more, and most preferably 100 μmol/g or more. If the amount of the 2,3-dihydroxypropyl group is less than 10 μmol/g, noise may increase as a result of an increase in non-specific adsorption of proteins and nucleic acids.

Possession of both the polyoxyethylene group and 2,3-dihydroxypropyl group ensures that organic polymer particles of this embodiment exhibits outstandingly high sensitivity, while maintaining excellent dispersibility resulting from the polyoxyethylene group and a low noise resulting from the 2,3-dihyroxypropyl group.

The number average particle diameter (hereinafter referred to simply as "particle diameter") of the organic polymer particles of this embodiment is preferably from 0.1 to 15 μm, more preferably from 0.3 to 10 μm, and most preferably from 1 to 10 μm. The particle diameter can be determined by the laser diffraction-scattering method. If the particle diameter is less than 0.1 μm, it takes a long time for separation using centrifugation and the like, resulting in insufficient separation of particles from a washing solvent such as water. This makes it difficult to sufficiently remove molecules other than target molecules (e.g. biological-related substances such as proteins and nucleic acids); possibly giving rise to inadequate purification. On the other hand, if the particle diameter is more than 15 μm, the sensitivity may be impaired as a result of a decrease in the amount of captured physiologically active substances due to a small specific surface area.

The organic polymer particles of this embodiment are usually used by dispersing in an appropriate dispersion medium. A dispersion medium not dissolving the organic polymer particles or not swelling the organic polymer particles are preferably used as the dispersion medium. An aqueous medium can be given as a preferable dispersion medium, for example. The aqueous medium here refers to water or a mixture of water and an organic solvent miscible with water (e.g. alcohols, alkylene glycol derivatives, etc.).

The contact angle of a dry coating film, which is made from a water dispersion of the organic polymer particles of this embodiment, and water is preferably 40° or less, more preferably 30° or less, and most preferably from 10° to 25°.

The dry coating film made from the water dispersion of the organic polymer particles can be obtained by preparing a water dispersion by dispersing 50 mg of the particles in 0.2 ml of purified water, applying this water dispersion to a flat and smooth substrate such as a glass slide using an applicator or the like, and drying the coating at a humidity of 40% and a temperature of 25° C. for 24 hours. The contact angle of the dry coating film with water can be determined by dropping about 1 μl of water drop on the dry coating film, immediately acquiring the image data from the horizontal direction using a camera, and measuring the angle between the outline of waterdrop and the horizon of the coating film, assuming that the outline of waterdrop is a part of a circle's perimeter. High sensitivity and low noise can be ensured at the same time by having the contact angle of a dry coating film made from a water dispersion of the organic polymer particles of this embodiment with water in the above ranges.

The contact angle of a dry coating film made from a water dispersion of the organic polymer particles of this embodiment with water can be adjusted by varying the types and amounts of the monomers (A) to (D), reactive emulsifier (R), and modifier (M) which will be described later.

4.1.2. Production of Organic Polymer Particles 4.1.2-1. Method for Introducing Polyoxyethylene Group As preferable methods for introducing the polyoxyethylene group in the production of the organic polymer particles in this embodiment, the following methods (i) to (iii) can be given, for example.

(i) A method of polymerizing the monomer part containing a monomer (A) having a polyoxyethylene group.

(ii) A method of polymerizing the monomer part in the presence of a reactive emulsifier (R) having a polyoxyethylene group.

(iii) A method of binding a modifier (M) having a polyoxyethylene group with organic polymer particles having a 2,3-dihydroxypropyl group.

In designing the particles, the above method (i) is a comparatively easy method because a decrease or increase of the amount of the monomer (A) having a polyoxyethylene group results in only a small variation of the particle diameter and it is unnecessary to increase the production steps.

The above method (ii) possesses merits of being able to introduce a comparatively fixed amount of polyoxyethylene groups and of not requiring an increase of production steps.

The above method (iii) has a merit of a high degree of freedom of the introduction amount.

The methods (i) to (iii) can be combined in accordance with to the objective. As the method for introducing a polyoxyethylene group other than the methods (i) to (iii), a method of using a polymerization initiator having a polyoxyethylene group, a method of using a chain transfer agent having a polyoxyethylene group, a method of polymerizing ethylene oxide by ring-opening on the surface of organic polymer particles, and the like can be given.

Specific examples and amounts of each component and polymerization methods for the above production methods (i) to (iii) will be described later.

4.1.2-2. Composition of Monomer Part

The organic polymer particles of this embodiment can be produced by forming a polymer part obtained by (co)polymerizing a monomer part having one or more types of monomer. Each of the monomers for forming the monomer part will now be described.

4.1.2-2a. Monomer (a) Having a Polyoxyethylene Group

The organic polymer particles of this embodiment are preferably obtained by (co)polymerizing a monomer part having a monomer (A) having a polyoxyethylene group (the above method (i)). The following monomers (A) to (D) of this embodiment are preferably radically polymerizable monomers.

As the monomer (A) having a polyoxyethylene group (hereinafter also referred to as "monomer (A)"), an acrylate or methacrylate having a polyoxyethylene group are preferable. Specific examples include Blemmer PE-90, PE-200, PE-350, PME-100, PME-200, PME-400, AE-350 (manufactured by NOF Corp.), MA-30, MA-50, MA-100, MA-150, RA-1120, RA-2614, RMA-564, RMA-568, RMA-1114, MPG130-MA (manufactured by Nippon Nyukazai Co., Ltd.), NK ECOMONOMER M-90G, AM-90G (manufactured by Shin-Nakamura Chemical Co., Ltd.), and the like.

The monomer (A) is used in the monomer part preferably in an amount from 0.1 to 10 parts by weight and particularly preferably from 0.5 to 3 parts by weight for 100 parts by weight of the monomer part. If the amount of the monomer (A) in the monomer part is less than 0.1 part by weight, dispersibility may be inferior, and if the amount exceeds 10 parts by weight, polymerization may become unstable. In the case in which the later described reactive emulsifier (R) or modifier (M) is used, the monomer (A) is not a necessary component. However, it is possible to use the monomer (A) together with the reactive emulsifier (R) and modifier (M).

4.1.2-2b. Monomer (B) Producing a 2,3-Dihydroxypropyl Group by Hydrolysis

The organic polymer particles of this embodiment are preferably formed by hydrolyzing particles comprising a polymer part obtained by copolymerizing a monomer part containing a monomer (B) producing a 2,3-dihydroxypropyl group by hydrolysis. Specifically, in this instance, the monomer part further comprises a monomer (B) which produces a 2,3-dihydroxypropyl group by hydrolysis. It is possible to introduce a larger amount of the 2,3-dihydroxypropyl group into the polymer part in a stable manner and to improve polymerization stability by using the monomer (B) which produces a 2,3-dihydroxypropyl group by hydrolysis in the above (co)polymerization, as compared with the case in which a monomer having a 2,3-dihydroxypropyl group before (co)polymerization is used.

Organic polymer particles having a hydroxyl group originating from a 2,3-dihydroxypropyl group and polyoxyethylene group can be obtained by, for example, using the above method (i) to form a polymer part by polymerizing a monomer part containing a monomer (A) having a polyoxyethylene group and a monomer (B) producing a 2,3-dihydroxypropyl group by hydrolysis, then hydrolyzing the polymer part.

As the monomer (B) producing a 2,3-dihydroxypropyl group by hydrolysis (hereinafter also referred to as "monomer (B)"), monomers wherein a hydroxyl group is protected by a known protecting group can be given, for example, (B-1) a monomer having a 2,3-epoxypropyl group, (B-2) a monomer obtained by acetalating a 2,3-dihydroxypropyl group, (B-3) a monomer obtained by silylating a 2,3-dihydroxypropyl group, and the like can be given. As specific examples of the (B-1) monomer having a 2,3-epoxypropyl group, glycidyl (meth)acrylate, allyl glycidyl ether, and the like can be given. As specific examples of the (B-2) monomer obtained by acetalating a 2,3-dihydroxypropyl group, 1,3-dioxolan-2-on-4-ylmethyl (meth)acrylate, 1,3-dioxolane-2,2-dimethyl-4-ylmethyl (meth)acrylate, and the like can be given. As specific examples of the (B-3) monomer obtained by silylating a 2,3-dihydroxypropyl group, di(t-butyl)silylated compound of 2,3-dihydroxypropyl (meth)acrylate, di(trimethylsilyl)ated compound of 2,3-dihydroxypropyl (meth)acrylate, and the like can be given.

Although the conditions for hydrolyzing the functional group of the monomer (B) depend on the type of the monomer (B), particles dispersed in water are usually stirred from several hours to several tens of hours while heating and using an acid, a base, or a fluoride as a catalyst to effect hydrolysis. It is possible to introduce a tosyl group while hydrolyzing by using p-toluenesulfonic acid as an acid. Tosylation of the organic polymer particles will be described later. In the hydrolysis of the functional group of the monomer (B), not all of the functional groups of the copolymer need to be hydrolyzed as long as storage stability and the like are not hindered. Although the hydrolysis of the functional group of the monomer (B) is usually conducted after polymerization of the monomer part, a portion of the functional group may be hydrolyzed during polymerization.

The monomer (B) is used in the monomer part preferably in an amount from 60 to 100 wt % and particularly preferably from 70 to 95 wt % for 100 wt % of the monomer part. If the amount of the monomer (B) in the monomer part is less than 60 wt %, noise may increase as a result of an increase in non-specific adsorption of proteins and nucleic acids.

4.1.2-2c. Crosslinkable Monomer (C)

The organic polymer particles of this embodiment preferably have a particle surface obtained by copolymerizing a crosslinkable monomer (C). In this instance, the monomer part further comprises a crosslinkable monomer (C).

The crosslinkable monomer (C) (hereinafter also referred to as "monomer (C)") is a monomer which can be copolymerized with other monomers of the monomer part and possesses two or more radically polymerizable unsaturated bonds in one molecule. As examples of the crosslinkable monomer (C), polyfunctional (meth)acrylates such as ethylene glycol diacrylate, ethylene glycol dimethacrylate, trimethylolpropane triacrylate, trimethylolpropane trimethacrylate, pentaerythritol triacrylate, pentaerythritol trimethacrylate, dipentaerythritol hexacrylate, dipentaerythritol hexamethacrylate; conjugated diolefins such as butadiene and isoprene; divinylbenzene, diallyl phthalate, allyl acrylate, allyl methacrylate, and the like can be given. As further examples of the crosslinkable monomer (C), hydrophilic monomers such as polyethylene glycol diacrylate, polyethylene glycol dimethacrylate, poly(meth)acrylates of polyvinyl alcohol, and the like can be given.

The amount of the crosslinkable monomer (C) is preferably from 0 to 30 wt % and particularly preferably from 5 to 20 wt % for 100 wt % of the monomer part. If the amount of the monomer (C) exceeds 30 wt %, the particles become porous, possibly causing non-specific adsorption to increase.

4.1.2-2d. Other Monomers (D)

The organic polymer particles of this embodiment may have a particle surface obtained by copolymerizing monomers (D) other than the above monomers (A) to (C) (other monomers (D)). As other monomers (D), monomers having a carboxyl group such as acrylic acid, methacrylic acid, maleic acid, and itaconic acid; (meth)acrylates having a hydrophilic functional group such as 2-hydroxyethyl acrylate, 2-hydroxyethyl methacrylate, methoxyethyl acrylate, and methoxyethyl methacrylate; hydrophilic monomers such as acrylamide, methacrylamide, N-methylolacrylamide, N-methylolmethacrylamide, and diacetoneacrylamide; aromatic vinyl monomers such as styrene, α-methylstyrene, and styrene halide; vinyl esters such as vinyl acetate and vinyl propionate; unsaturated nitriles such as acrylonitrile; and ethylenically unsaturated alkyl carboxylate such as methyl acrylate, methyl methacrylate, ethyl acrylate, ethyl methacrylate, butyl acrylate, butyl methacrylate, 2-ethylhexyl acrylate, 2-ethylhexyl methacrylate, lauryl acrylate, lauryl methacrylate, stearyl acrylate, stearyl methacrylate, cyclohexyl acrylate, cyclohexyl methacrylate, isobornyl acrylate, and isobornyl methacrylate can be given. As the method for introducing the carboxyl group, a method of copolymerizing an ester monomer having a carboxyl group protected by alcohol such as tert-butyl (meth)acrylate, 1-methylcyclopentyl (meth)acrylate, 1-ethylcyclopentyl (meth)acrylate, 1-methylcyclohexyl (meth)acrylate, 1-ethylcyclohexyl (meth)acrylate, 2-methyladamantan-2-yl (meth)acrylate, 2-ethyladamantan-2-yl (meth)acrylate, tetrahydrofuranyl (meth) acrylate, and tetrahydropyranyl (meth)acrylate; a cyclic ester monomer such as α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, and α-methacryloyloxy-α-methyl-γ-butyrolactone; and an acid anhydride such as maleic anhydride and itaconic anhydride, followed by hydrolysis can be used. The 2,3-dihydroxypropyl group can be introduced using a monomer having a non-protected 2,3-dihydroxypropyl group such as 2,3-dihydroxypropyl (meth)acrylate as the other monomer (D). The amount of the other monomers (D) used is a balance to the above monomers (A) to (C).

4.1.2-3 Reactive Emulsifier (R) Having a Polyoxyethylene Group

The organic polymer particles of this embodiment are preferably obtained by (co)polymerizing the monomer part in the presence of a reactive emulsifier (R) having a polyoxyethylene group (hereinafter also referred to as "reactive emulsifier (R)") (the above method (ii)).

For example, using the above method (ii), organic polymer particles having a hydroxyl group originating from a 2,3-dihydroxypropyl group and polyoxyethylene group can be obtained by a step of forming a polymer part by polymerizing a monomer part having a monomer (B) producing a 2,3-dihydroxypropyl group by hydrolysis in the presence of a reactive emulsifier having a polyoxyethylene group (R), and a step of hydrolyzing the polymer part.

The reactive emulsifier (R) of the invention is an emulsifier that is reactive with a component contained in the monomer part. As specific examples, an emulsifier having a hydrophobic group such as an alkyl group having eight or more carbon atoms, a hydrophilic group having a polyoxyethylene chain, and a radically polymerizable unsaturated double bond in one molecule can be given. As mentioned before, the end of the polyoxyethylene chain may be substituted with a functional group.

As the reactive emulsifier (R) of which the end is not substituted, a nonionic surfactant copolymerizable with an ethylenically unsaturated monomer can be given, for example, α-[(allyloxy)methyl]-2-(nonylphenoxy)ethyl]-ω-hydroxypolyoxyethylene such as ADEKA REASOAP NE-20, NE-30, and NE-40 (manufactured by ADEKA Corp.), polyoxyethylene alkylpropenylphenyl ether such as Aqualon RN-10, RN-20, RN-30, RN-50 (manufactured by Dai-ichi Kogyo Seiyaku Co., Ltd.), and the like. As examples of the reactive emulsifier (R) of which the end is substituted, Eleminol JS-2, JS-5 (manufactured by Sanyo Chemical Industries, Ltd.), Latemul S-120, S-180A, S-180, PD-104 (manufactured by KAO Corp.), Aqualon HS-10, HS-20, KH-10 (manufactured by Dai-ichi Kogyo Seiyaku Co., Ltd.), ADEKA REASOAP SE-10N, SR-10 (manufactured by ADEKA Corp.), and like can be given. These reactive emulsifiers (R) can be used either individually or in combination of two or more.

The reactive emulsifier (R) is used preferably in an amount from 0.1 to 10 parts by weight and particularly preferably from 0.5 to 3 parts by weight for 100 parts by weight of the monomer part. If the reactive emulsifier (R) is used in an amount less than 0.1 part by weight, dispersibility may become inferior, and if the amount exceeds 10 parts by weight, particles having a very small particle size may be formed. In the case in which the monomer (A) and later described modifier (M) are used, the reactive emulsifier (R) is not a necessary component. However, it is possible to use the reactive emulsifier (R) together with the monomer (A) and modifier (M).

4.1.2-4. Modifier (M) Having a Polyoxyethylene Group and Method of Modification

The organic polymer particles of this embodiment are preferably formed by binding a modifier (M) having a polyoxyethylene group (hereinafter also referred to as "modifier (M)") to organic polymer particles having a 2,3-dihydroxypropyl group (above method (iii)). The modifier (M) may be bound after being bonded with the later-described probe.

The organic polymer particles having a 2,3-dihydroxypropyl group can be obtained by polymerizing a monomer part containing a monomer (B) which produces a 2,3-dihydroxypropyl group by hydrolysis to form particles having a polymer part and hydrolyzing the polymer part.

The modifier (M) of the invention is a molecule having a functional group which can bond with organic polymer particles and a polyoxyethylene group. The type of the functional group which can bond with the organic polymer particles to be used varies according to the functional group to be introduced in the surface of the organic polymer particles.

As the functional group of the modifier (M), an amino group can be given as an example. In this instance, a carboxyl group can be introduced into the organic polymer particles and coulomb bonded with the amino group of the modifier (M) to produce organic polymer particles having a hydroxyl group originating from a 2,3-dihydroxypropyl group and a polyoxyethylene group. The organic polymer particles having a hydroxyl group originating from a 2,3-dihydroxypropyl group and a polyoxyethylene group can also be produced by introducing a carboxyl group into the organic polymer particles followed by activating the carboxyl group with a known activator such as a water-soluble carbodiimide to initiate amide binding of the carboxyl group with the amino group of the modifier (M).

As another method for producing the organic polymer particles having a hydroxyl group originating from a 2,3-dihydroxypropyl group and a polyoxyethylene group, a method of tosylating a portion of a 2,3-dihydroxypropyl group of organic polymer particles and substituting with the amino group of the modifier (M) to cause bonding can be given. Still another method for producing the organic polymer particles having a hydroxyl group originating from a 2,3-dihydroxypropyl group and a polyoxyethylene group comprises introducing an epoxy group into organic polymer particles and bonding the epoxy group with an amino group of the modifier (M).

It is preferable that the amino group of the modifier (M) be introduced at one end of the polyoxyethylene chain and more preferably 2 to 20 groups of the amino group at one end of the polyoxyethylene chain.

As an example of the functional group of the modifier (M), a mercapto group can be given. It is preferable that the mercapto group of the modifier (M) be introduced at one end of the polyoxyethylene chain. In this instance, the organic polymer particles having a hydroxyl group originating from a 2,3-dihydroxypropyl group and a polyoxyethylene group can be produced by tosylating a portion of a 2,3-dihydroxypropyl group of organic polymer particles and substituting with the mercapto group of the modifier (M) to cause binding. Still another method for producing the organic polymer particles having a hydroxyl group originating from a 2,3-dihydroxypropyl group and a polyoxyethylene group comprises introducing an epoxy group into organic polymer particles and bonding the epoxy group with a mercapto group of the modifier (M).

As a further example of the functional group of the modifier (M), an epoxy group can be given. It is preferable that the epoxy group of the modifier (M) be introduced at one end of the polyoxyethylene chain. In this instance, a carboxyl group or amino group is introduced into the organic polymer particles and bonded with the epoxy group of the modifier (M) to produce organic polymer particles having a hydroxyl group originating from a 2,3-dihydroxypropyl group and a polyoxyethylene group.

As other combinations of modifier (M) functional group/organic polymer particles functional group, silyl group/hydroxyl group, carbonyl group/hydrazide group, biotin group/avidin group, and the like can be given.

As a most preferable example, a method of introducing a carboxyl group into the organic polymer particles and coulomb bonding the carboxyl group with the amino group of the modifier (M) of the following formula (1) to produce organic polymer particles having a hydroxyl group originating from a 2,3-dihydroxypropyl group and a polyoxyethylene group can be given.

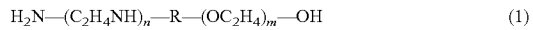

$$H_2N-(C_2H_4NH)_n-R-(OC_2H_4)_m-OH \qquad (1)$$

wherein, n=2 to 20, m=2 to 200, and R is a divalent hydrocarbon group such as phenylene, alkylene, and the like.

4.1.2-5. Polymerization Method

The organic polymer particles of this embodiment may be produced by a conventional method such as emulsion polymerization, soap-free polymerization, and suspension polymerization. Specifically, the organic polymer particles of this embodiment may be obtained by, for example, suspension polymerization of the above vinyl monomer or polymer bulk shattering. For example, the organic polymer particles of this embodiment can be obtained by the two-step swelling polymerization method using seed particles (mother particles) described in JP-B-57-24369, the polymerization method described in J. Polym. Sci., Polymer Letter Ed., 21, 937 (1983), and the methods described in JP-A-61-215602, JP-A-61-215603, and JP-A-61-215604. Of these, the two-step swelling polymerization method using seed particles (mother particles) is preferable for reducing the coefficient of particle size variation. Polystyrene or a styrene-based copolymer can be used as seed particles (mother particles). The polymer part added by the two-step swelling polymerization method consists of a copolymer of monomers (A) to (D).

As the emulsifier used when copolymerizing the monomers (A) to (D), in addition to the above reactive emulsifiers, for example, anionic surfactants such as alkyl sulfate, alkylaryl sulfate, alkyl phosphate, and fatty acid salts; cationic surfactants such as alkylamine salt and alkyl quaternary amine; nonionic surfactants such as polyoxyethylene alkyl ether, polyoxyethylene alkylaryl ether, and block type polyethers; and amphoteric surfactants such as carboxylic acid-type surfactants (e.g. amino acids, betaine acids, and the like) and sulfonic acid-type surfactants can be given. These emulsifiers can be used either individually or in combination of two or more. Although there are no specific limitations to the amount of the emulsifier to be used, the amount is usually from 0.1 to 50 parts by weight, preferably from 0.2 to 20 parts by weight, and particularly preferably from 0.5 to 5 parts by weight for 100 parts by weight of the monomers (A) to (D). An amount less than 0.1 part by weight is not preferable due to insufficient emulsification and decline in stability during radical polymerization. On the other hand, an amount exceeding 50 parts by weight is not desirable due to a problem of foaming.

As the radical polymerization initiator used in the copolymerization of monomers (A) to (D), persulfates such as potassium persulfate, sodium persulfate, and ammonium persulfate; water-soluble initiators such as hydrogen peroxide, t-butyl hydroperoxide, t-butylperoximaleic acid, peroxide succinate, and 2,2'-azobis[2-N-benzylamidino]propane hydrochloride; oil-soluble initiators such as benzoyl peroxide, cumene hydroperoxide, diisopropyl peroxydicarbonate, cumyl peroxyneodecanoate, cumyl peroxyoctanoate, and azobisisobutyronitrile; redox initiators using reducing agents such as acidic sodium sulfite, rongalite, and ascorbic acid; and the like can be given. As the radical polymerization initiator, an oil-soluble initiator which does not exhibit acidity or basicity in water is preferable.

4.2. Organic Polymer Particles Containing Magnetic Material and Process for Producing Same The organic polymer particles of this embodiment may be organic polymer particles containing a magnetic material fine magnetic material particles (hereinafter referred to as "magnetic material-containing organic polymer particles"). The fine magnetic material particles described in the above first embodiment can be used as the magnetic material for this embodiment. Because the magnetic material-containing organic polymer particles can be separated using a magnet without using centrifugation, for example, a step for separating particles from samples to be inspected can be simplified or automated.

Magnetic material-containing organic polymer particles include (I) particles comprising a continuous phase of a non-magnetic material such as an organic polymer with fine magnetic material particles being dispersed therein, (II) particles comprising a core of a secondary aggregate of fine magnetic material particles and a shell of non-magnetic material such as an organic polymer, (III) particles comprising mother particles, which comprises nuclear particles of a non-magnetic material such as an organic polymer and a secondary aggregate layer (a magnetic material layer) of fine magnetic material particles provided on the surface of the nuclear particles, as a core, and an outermost organic polymer layer of the mother particles, as a shell, and the like. In (I) to (III), the non-magnetic material of the organic polymer and the like is equivalent to the above-described "polymer part". Of these, (III) particles consisting of a core of the mother particles containing a secondary aggregate layer of fine magnetic material particles and a shell of an organic polymer layer (polymer part) are preferable. The interface between the nuclear particles and the outer layer (a magnetic material layer) and the interface between the magnetic material layer and its outer layer (a polymer part) may be in a state in which the components of both layers are present together.

The organic polymer (polymer part) used for the magnetic material-containing organic polymer particles with various structures, specifically the polymer forming the outermost surface of the particles, excluding a core portion of core-shell type particles, must have a polyoxyethylene group and a 2,3-dihydroxypropyl group.

The most preferable magnetic material-containing organic polymer particles have a polymer (polymer part) having a hydroxyl group originating from a 2,3-dihydroxypropyl group and a polyoxyethylene group covering mother particles containing nuclear particles and a magnetic material layer of superparamagnetic fine particles formed on the surface of the nuclear particles. In this instance, the magnetic material-containing organic polymer particles comprise the mother particles as cores and the polymer having a hydroxyl group originating from a 2,3-dihydroxypropyl group and a polyoxyethylene group (polymer part) as shells.

The polymer having a hydroxyl group originating from a 2,3-dihydroxypropyl group and a polyoxyethylene group can be obtained from the above-described production method. Specifically, the polymer having a hydroxyl group originating from a 2,3-dihydroxypropyl group and a polyoxyethylene group is obtained by hydrolysis of a copolymer obtained by copolymerizing a monomer part comprising 0 to 10 parts by weight of a monomer (A) having a polyoxyethylene group, 60 to 100 parts by weight of a monomer (B) which produces a 2,3-dihydroxypropyl group by hydrolysis, 0 to 30 parts by weight of a crosslinkable monomer (C), and 0 to 40 parts by weight of other monomers (D). Hydrolysis may be conducted during polymerization.

As the method for producing mother particles with a magnetic material layer of superparamagnetic fine particles on the outside of nuclear particles, the method described in the above first embodiment can be given, for example. Fine particles of ferrite and/or magnetite with a particle diameter of 5 to 20 nm, for example, can be preferably used as the superparamagnetic fine particles used in organic polymer particles of this embodiment.

The polymer part (shell) can be formed by copolymerizing the monomer part obtained from the above monomers (A) to (D) in the presence of the above-mentioned mother particles (core). The monomer components used are as described above. A more specific method of polymerization is disclosed in JP-A-2004-205481 and the like. The conditions for hydrolysis treatment after the polymerization are also the same as described above. Magnetic material-containing organic polymer particles are preferably hydrolyzed under weakly acidic to basic conditions because hydrolysis under strongly acidic conditions may dissolve the superparamagnetic fine particles.

In order to inhibit dissolution of the superparamagnetic fine particles on the mother particles, the magnetic material-containing organic polymer particles may be formed after forming a coating layer on the surface of mother particles comprising nuclear particles with a magnetic material layer of superparamagnetic fine particles formed on the surface using another monomer part comprising 0 to 30 parts by weight of crosslinkable monomer (C) and 70 to 100 parts by weight of other monomers (D), by copolymerizing the monomer part obtained from the monomers (A) to (D) using these mother particles having the coating layer as cores to obtain particles with polymer part (shells), followed by hydrolysis of the resulting particles. In the case of hydrolyzing the magnetic material-containing organic polymer particles in which the superparamagnetic fine particles are covered with a coating layer in this manner, a broader hydrolysis conditions from a strongly acidic to strongly basic conditions can be selected.

It is desirable to remove residual hydrolysis catalysts from the dispersions of the organic polymer particles after hydrolysis and magnetic material-containing organic polymer particles by repeatedly washing these particles with water by a centrifugal separation method or a magnetic separation method.

4.3. Organic Polymer Particles for Probe Binding and Probe-Bound Particles

The organic polymer particles for probe binding. of one embodiment of the invention contain a tosyl group. More specifically, the organic polymer particles for probe binding of this embodiment are obtained by tosylating organic polymer particles having a polyoxyethylene group and a 2,3-dihydroxypropyl group at least on the surface of the particles. More specifically, the organic polymer particles for probe binding of this embodiment may have a reactive group obtained by tosylating at least one of the hydroxyl group at the end of the polyoxyethylene group and the 2,3-dihydroxypropyl group on the surface of the particles.

The reactive group obtained by tosylating a 2,3-dihydroxypropyl group is, for example, a group in which one or both hydroxyl groups of a 2,3-dihydroxypropyl group are tosylated, with specific examples including a 2-hydroxy-3-(4'-methylphenyl)sulfonyloxypropyl group, 3-hydroxy-2-(4'-methylphenyl)sulfonyloxypropyl group, and 2,3-di(4'-methylphenyl)sulfonyloxypropyl group. The organic polymer particles for probe binding of this embodiment may contain a 2,3-dihydroxypropyl group that has not been tosylated.

The organic polymer particles for probe binding of this embodiment may be chemically bonded with a primary probe through the (4'-methylphenyl)sulfonyl group, specifically the tosyl group, in order to obtain probe-bound particles for immunoassay. The probe-bound organic polymer particles obtained by washing out the excess amount of the primary probe can exhibit outstandingly high sensitivity and low noise due to 2,3-hydroxypropyl groups remaining after deactivating the unreacted tosyl groups. This effect is not expressed by particles having only a group obtained by tosylating a monohydroxypropyl group, for example, by particles possessing only a 3-(4'-methylphenyl)sulfonyloxypropyl group.

Tosylation can be conducted using a conventional method. For example, tosylation can be achieved by reacting the 2,3-dihydroxypropyl group of the organic polymer particles with p-toluenesulfonate thereby converting the 2,3-dihydroxypropyl group into a 2-hydroxy-3-(4'-methylphenyl)sulfonyloxypropyl group. Although there are no specific limitations to the p-toluenesulfonate, p-toluenesulfonate chloride and the like can be given as examples. As another method for achieving tosylation, a method comprising reacting the functional group originating from the monomer (B) before hydrolysis or the functional group originating from the remaining monomer (B) after hydrolysis with p-toluenesulfonic acid can be given. In this procedure, after dispersing the organic polymer particles in an organic solvent such as pyridine, p-toluenesulfonic acid chloride or p-toluenesulfonic acid is added in an amount from 1 to 50 parts by weight for 100 parts by weight of the organic polymer particles and reacted at room temperature for 1 to 6 hours. Alternatively, the above-mentioned tosylation may be conducted by condensing the 2,3-dihydroxypropyl group of the organic polymer particles and p-toluenesulfonic acid by dehydration to convert the 2,3-dihydroxypropyl group into a 2-hydroxy-3-(4'-methylphenyl)sulfonyloxypropyl group.

In this procedure of tosylating the organic polymer particles, both of the hydroxyl groups of one 2,3-dihydroxypropyl group may be tosylated or only one of the hydroxyl groups of one 2,3-dihydroxypropyl group may be tosylated. It is sufficient that at least a portion of a number of 2,3-dihydroxypropyl groups in the organic polymer particles are tosylated. Furthermore, in the tosylating of the organic polymer particles, hydroxyl groups of functional groups of the organic polymer particles other than the 2,3-dihydroxypropyl groups may also be tosylated. It is sufficient that part of hydroxyl groups among the hydroxyl groups of the 2,3-dihydroxypropyl groups in the organic polymer particles remain without being tosylated.

The organic polymer particles for probe binding of this embodiment can be obtained by the above methods. The dispersion of the organic polymer particles for probe binding is preferably repeatedly washed with acetone and water by a centrifugal separation method or a magnetic separation method in order to obtain a water dispersion of organic polymer particles for probe binding.

Because a tosyl group has been introduced into the surface of the particles for probe binding of this embodiment, a primary probe can be chemically bound on the surface of the particles by merely mixing the primary probe and the particles during actual use.

After binding the primary probe onto the surface of the particles, an excess amount of the primary probe is washed out and unreacted tosyl groups are deactivated as required. As the deactivator, deactivators having a hydroxyl group such as ethanolamine and tris(hydroxyamino)methane are preferably used. In addition, a polyoxyethylene group can be introduced in this procedure by using the above modifier (M) as the deactivator. A tosyl group may be hydrolyzed under acidic or alkaline conditions in a range which does not hinder the activity of the primary probe. Although a conventional blocking operation is not required after binding the primary probe onto the surface of the particles, a blocking agent such as albumin may be used in the above deactivation step. A conventional analytical procedure using the particles may follow.

4.4. Use

As the use of the organic polymer particles of this embodiment, those mentioned in connection with the organic polymer particles of the first embodiment can be given. For example, the particles can be used as an affinity carrier such as particles for chemical compound-binding carrier in the biochemical field, particles for chemical-binding carrier for diagnostics, and the like, particularly can exhibit remarkably high sensitivity and low noise as probe-bound particles for immunoassay bound with a primary probe such as an antigen or an antibody.

In the probe-bound particles of this embodiment, the substances to be inspected are biological-related substances and chemical compounds which are contained in immunoassay reagents and inspection samples.

As the target biological-related substances and chemical compounds for inspection, those previously described in the first embodiment can be given, for example.

The probe-bound particles of this embodiment are obtained by mixing the above organic polymer particles for probe binding with primary probes and particles.

As another method for obtaining the probe-bound particles of this embodiment, a method comprising introducing carboxyl groups into the surface of organic polymer particles, activating the carboxyl groups using a known activator such as a water-soluble carbodiimide, and mixing the primary probe and the particles can be used. After binding the primary probe onto the surface of the particles, an excess amount of the primary probe is washed out and unreacted activated carboxyl groups are deactivated as required. In addition, after the primary probe is bound onto the surface of the particles, a conventional blocking operation may be conducted or a blocking agent such as albumin may be used in the deactivation step. A conventional analytical procedure using the particles may follow.

Proteins (antigens or antibodies) or nucleic acids are used as a probe to be carried on the particles for probe binding of this embodiment. Of these, antigens and antibodies are preferable probes. In this case, there are no specific limitations to the antigens and antibodies inasmuch as the antigen or antibody reacts with components commonly contained in samples to be assayed, for example, the examples given in the above first embodiment can be given.

The organic polymer particles of this embodiment can also be used as an affinity carrier for sensing proteins such as an enzyme and hormone, nucleic acids such as a DNA and RNA, lipids, and physiologically active sugar chain compounds on the surface of particles by a chemical bonding method. In addition, the organic polymer particles of this embodiment can be used for selecting and purifying proteins and the like (target molecules) exhibiting specific interactions with a target chemical compound for analysis by immobilizing the chemical compound (chemical compound for analysis: ligand molecules) by chemical bonding and analyzing and/or measuring the specific interactions using specific interactions with proteins and the like.

The ligand molecules to be bound with the particles are not specifically limited insofar as such a ligand molecule has a functional group which can react with at least one of the polyoxyethylene group or 2,3-dihydroxypropyl group possessed by the organic polymer particles of this embodiment, specific examples include nucleic acid, peptide nucleic acid, hormone, proteins having a molecular weight of 500 to 1,000,000, sugar chain, polysaccharide, cell, aptamer, virus, enzyme, various types of tag capturing substances for affinity, coenzymes such as biotin, and chemical compounds having a particular physiologically active effect (or may have a particular physiologically active effect).

The organic polymer particles and probe-bound particles of this embodiment may be suitably used in particles used in biochips, for example, the biochips disclosed in JP-A-2005-148048.

5. Examples

The invention will now be described in more detail by way of examples, which should not be construed as limiting the invention. In Examples 1 to 4, "%" and "part" are indicated on the weight basis.

5.1. Example 1

5.1.1. Evaluation Method

5.1.1-1. CLEIA (Chemiluminescence enzyme immunity assay)

10 µl of particle dispersions (equivalent to 50 µg of particles) obtained in the later-described Experimental Examples and Comparative Experimental Examples, sensitized with an anti-AFP (α-fetoprotein) antibody, were taken in a test tube and mixed with 50 µl of a standard sample of an AFP antigen (manufactured by NIPPON BIOTEST LABO.) diluted to a concentration of 100 ng/ml with fetal calf serum (FCS). The mixture was reacted at 37° C. for 10 minutes. After centrifugation to separate particles and after removing the supernatant liquid, 40 µl of an anti-AFP antibody (a reagent attached to "Lumipulse AFP-N" manufactured by Fujirebio Inc.), labeled with an alkali phophataze (hereinafter referred to as "ALP") as a secondary antibody, was added, followed by a reaction at 37° C. for 10 minutes. Next, after centrifugation to separate particles and removing the supernatant liquid, the resulting particles were washed three times by centrifugation using PBS and dispersed in 50 µl of 0.01% Tween 20. The resulting dispersion was transferred to a new tube. After the addition of 100 µl of an ALP substrate solution (Lumipulse substrate solution manufactured by Fujirebio Inc.), the mixture was reacted at 37° C. for 10 minutes to measure the amount of chemiluminescence. A chemiluminescence luminometer ("Lumat LB9507" manufactured by Berthold Japan, Co., Ltd.) was used for measuring the chemiluminescence.

5.1.1-2. Particle Size

The number average particle diameter of the particles and the coefficient of variation were measured using a laser diffraction particle size distribution analyzer ("SALD-200V" manufactured by Shimadzu Corp.).

5.1.1-3. Contact Angle of Dry Coating Film Obtained from Water Dispersion with Water 50 mg of the organic polymer particles obtained in the later-described Synthesis Examples and Comparative Synthesis Examples were washed ten times with 1 ml of purified water and finally dispersed in 0.2 ml of purified water to prepare water dispersions. The water dispersions were applied to sheets of glass slide using an applicator and dried at a humidity of 40% and a temperature of 25° C. for 24 hours to obtain dry coatings. The contact angle of the dry coating films with water was measured using an FAMAS contact angle measurement system ("Drop Master 900" manufactured by Kyowa Interface Science Co., Ltd. according to the following method. An image data of water drops was acquired from the horizontal direction using a camera at 0.15 seconds after dropping 1.0 µl of water drops onto the dry coating film to determine the contact angle of the dry coating film with water from the angle between the outline of the water drop and the horizon of the coating film, assuming that the outline of water drop is a part of a circle's perimeter.

5.1.1-4. Carboxyl Group Content

The apparent amount of surface charges was calculated using a water dispersion containing 1 g of particles (solid component) by conductmetric titration described in JP-A-10-270233. The amount of charges of background was calculated in the same manner using only the dispersion medium (water). The carboxyl group content of the particles was determined from the differences of the resulting amounts of charges.

5.1.2. Synthesis Example 1 (Synthesis of Organic Polymer Particles Containing No Magnetic Material, Example in which Neither Monomer (A) Nor Monomer (B) is Used)

Organic polymer particles containing no magnetic material were prepared by the two-step swelling polymerization method using seed particles (mother particles) described below. Using polystyrene particles with a particle size of 0.98 µm obtained by soap-free polymerization as seed particles, a water dispersion (solid component amount: 5.0 g) was prepared by dispersing these polystyrene particles in 500 g of water in nitrogen atmosphere. An organic solvent (0.1 g of "Shellsol TK") was added to the seed particles in the first step, and, 5 g of methacrylic acid, which is a monomer (A') having a carboxyl group, 50 g of glycerol methacrylate (GLM), which is a monomer (B') having a 2,3-dihydroxypropyl group, 10 g of ethylene glycol dimethacrylate (EDMA), which is a crosslinkable monomer (C), and 35 g of methyl methacrylate (MMA), which is monomer (D) were added to the seed particles in the second step, and all of the monomers are caused to be absorbed. Then, 2 g of AIBN (azobisisobutyronitrile) was added, and the mixture was slowly stirred at 75° C. for 24 hours to obtain a polymer part. The reaction solution was cooled and filtered through a 500 mesh wire gauze to confirm that 97% of the product passed through the wire gauze. The polymerization stability was rather poor. The polymerization yield was 95%. The particles were washed with distilled water by centrifuge separation to obtain organic polymer particles (organic polymer particles with low non-specific adsorptivity) comprising mother particles as a core and the polymer part as a shell. The resulting organic polymer particles are designated as particles (i).

The particle diameter of the particles (i) was 2.5 µm, the carboxyl group content was 12 µmol/g, and the contact angle of a dry coating film made from the water dispersion with water was 38°.

5.1.3. Synthesis Example 2 (Synthesis of Organic Polymer Particles Containing No Magnetic Material, Example in which Both Monomer (A) and Monomer (B) are Used)

The polymerization reaction was carried out in the same two-step swelling polymerization method as in Synthesis Example 1 to form a copolymer covering the core of mother particles, except for adding 20 g of t-butyl (meth)acrylate (tBMA), which is a monomer (A), 70 g of glycidyl methacrylate (GMA), which is a monomer (B), and 10 g of EDMA, which is a monomer (C), in the second step. Subsequently to the polymerization reaction, 60 ml of 2 N sulfuric acid was added and the mixture was stirred at 60° C. for 6 hours to effect a hydrolysis reaction, thereby obtaining organic polymer particles (organic polymer particles exhibiting low non-specific adsorption) comprising mother particles as a core and the polymer part as a shell. The mixture was cooled to room temperature and neutralized with an aqueous solution of sodium hydroxide. The reaction mixture was filtered through a 500 mesh wire gauze to confirm that 99% of the mixture passed through the wire gauze. The polymerization stability was good. The polymerization yield was 99%. The particles were washed with distilled water by centrifugation. The resulting organic polymer particles are designated as particles (ii).

The particle diameter of the particles (ii) was 2.6 µm, the carboxyl group content was 24 µmol/g, and the contact angle of a dry coating film made from the water dispersion with water was 22°.

5.1.4. Synthesis Example 3 (Synthesis of Organic Polymer Particles Containing Magnetic Material)

2 parts by mass of 75% di(3,5,5-trimethylhexanoyl) peroxide solution ("Peroyl 355-75(S)" manufactured by NOF Corp.) and 20 parts by mass of 1% aqueous solution of sodium dodecylsulfate were mixed and finely emulsified using an ultrasonic dispersion equipment. The emulsion was added to a reactor containing 13 parts by mass of polystyrene particles with a particle size of 0.77 μm and 41 parts by mass of water and the mixture was stirred at 25° C. for 12 hours. In another vessel, 96 parts by mass of styrene and 4 parts by mass of divinylbenzene were emulsified in 400 parts by mass of 0.1% aqueous solution of sodium dodecylsulfate. The resulting emulsion was added to the above reactor. After stirring at 40° C. for two hours, the mixture was heated to 75° C. and polymerized for 8 hours. After cooling to room temperature, particles were separated by centrifugation, washed with water, dried, and ground. The ground particles were used as nuclear particles (preparation of nuclear particles). The number average particle diameter was 1.5 μm.

Next, ferrite-type fine magnetic material particles (average primary particle diameter: 0.01 μm) with a hydrophobized surface were prepared by adding acetone to an oily magnetic fluid ("EXP series" manufactured by Ferrotec Corp.) to obtain a precipitate of the particles and drying the precipitate.

Then, 15 g of the above nuclear particles and 15 g of the hydrophobized fine magnetic material particles were thoroughly mixed in a mixer. The mixture was processed by a hybridization system ("Type NHS-0" manufactured by Nara Machinery Co., Ltd.) at a peripheral speed of blades (stirring blades) of 100 n/sec (16,200 rpm) for 5 minutes to obtain mother particles with a number average particle diameter of 2.0 μm, having a magnetic material layer of fine magnetic material particles on the surface.

A 1 l separable flask was charged with 375 g of an aqueous solution of 0.25 wt % of sodium dodecylbenzenesulfonate and 0.25 wt % of a nonionic emulsifying agent ("Emulgen 150" manufactured by Kao Corp.), followed by the addition of 15 g of the mother particles having a magnetic material layer prepared above. The mother particles were dispersed using a homogenizer and heated to 60° C. Next, a pre-emulsion, prepared by dispersing 27 g of MMA, 3 g of trimethylolpropane trimethacrylate (TMP), and 0.6 g of di(3,5,5-trimethylhexanoyl) peroxide ("Peroyl 355" manufactured by NOF Corp.) in 150 g of an aqueous solution of 0.25 wt % of sodium dodecylbenzenesulfonate and 0.25 wt % of a nonionic emulsifying agent ("Emulgen 150" manufactured by Kao Corp.), was dripped to the above 500 ml separable flask controlled at 60° C. over one and half hours. After dripping, the mixture was stirred for one hour while maintaining it at 60° C. Then, a pre-emulsion, prepared by dispersing 3 g of tBMA, which is a monomer (A), 10.5 g of GMA, which is a monomer (B), 1.5 g of TMP, which is a monomer (C), and 0.3 g of di(3,5,5-trimethylhexanoyl) peroxide ("Peroyl 355" manufactured by NOF Corp.) in 75 g of an aqueous solution of 0.25 wt % of sodium dodecylbenzenesulfonate and 0.25 wt % of a nonionic emulsifying agent ("Emulgen 150" manufactured by Kao Corp.), was dripped to the above 1 l separable flask controlled at 60° C. over one and half hours. After heating to 75° C., the polymerization was continued for two hours before completing the reaction. A copolymer covering cores of mother particles was prepared by the above process. Next, 60 ml of 1 mol/l sulfuric acid was added to the 1 l separable flask and the mixture was stirred at 60° C. for 6 hours to effect a hydrolysis reaction, thereby obtaining organic polymer particles (organic polymer particles exhibiting low non-specific adsorption) comprising mother particles as a core and the polymer part as a shell. The particles in the separable flask were magnetically separated and repeatedly washed with distilled water. A dispersion of the organic polymer particles containing magnetic material was obtained in this manner. The resulting particles are designated as particles (iii).

The particle diameter of the particles (iii) was 2.8 μm, the carboxyl group content was 24 μmol/g, and the contact angle of a dry coating film made from the water dispersion with water was 20°.

5.1.5. Comparative Synthesis Example 1 (Synthesis of Organic Polymer Particles Not Containing 2,3-dihydroxypropyl Group)

The polymerization reaction was carried out in the same manner as in Synthesis Example 1 except for using 2-hydroxyethyl methacrylate instead of GLM. The reaction solution was cooled and filtered through a 500 mesh wire gauze to confirm that 98% of the product passed through the wire gauze. The polymerization stability was rather poor. The polymerization yield was 96%. The particles were washed with distilled water by centrifugation. The resulting organic polymer particles of Comparative Synthesis Example 1 are designated as particles (i').

The particle diameter of the particles (i') was 2.5 μm, the carboxyl group content was 12 μmol/g, and the contact angle of a dry coating film made from the water dispersion with water was 92°.

5.1.6. Comparative Synthesis Example 2 (Synthesis of Organic Polymer Particles not Containing Carboxyl Group)

The polymerization reaction was carried out according to the same two-step swelling polymerization method as in Synthesis Example 2 except for using styrene instead of tBMA. The polymer was cooled to room temperature without conducting the hydrolysis reaction. The reaction mixture was filtered through a 500 mesh wire gauze to confirm that 99% of the mixture passed through the wire gauze. The polymerization stability was good. The polymerization yield was 99%. The particles were washed with distilled water by centrifugation. The resulting organic polymer particles of Comparative Synthesis Example 2 are designated as particles (ii').

The particle diameter of the particles (ii') was 2.5 μm, the carboxyl group content was 0 μmol/g, and the contact angle of a dry coating film made from the water dispersion with water was 48°.

5.1.7. Experimental Example 1

An aqueous solution of 1-ethyl-3-dimethylaminopropyl-carbodiimide hydrochloride (manufactured by Dojindo Laboratories, Inc.) was added to a water dispersion of 10 mg of particles (i) with a solid concentration of 1%. The mixture was stirred by rotation stirring at room temperature for two hours to activate carboxyl groups. Next, 100 μg of an antibody (an anti-AFP antibody, manufactured by Cosmo Bio Co., Ltd.) to human α-fetoprotein (AFP), which is a tumor marker, was added and the mixture was reacted at room temperature for 18 hours. After the reaction, the particles were separated by centrifugation, repeatedly washed with a washing solution (25 mmol/l Tris-HCl, 7.4 pH, containing 0.01% Tween 20), and diluted with the washing solution to a particle concentration of 0.5% to obtain probe-bound particles (particles for immunoassay) with an anti-AFP antibody bound as a primary probe. The chemiluminescence enzyme immunity assay (CLEIA) was carried out using the probe-bound particles. The noise intensity of the sample which not containing AFP was 255 RIU (Relative intensity unit). The signal intensity of the sample when the AFP concentration was 10 ng/ml was 17,747 (RIU).

5.1.8. Experimental Example 2

CLEIA was conducted in the same manner as in Experimental Example 1 except that particles (ii) were used instead of particles (i). The noise intensity of the sample which not containing AFP was 162 (RIU). The signal intensity of the sample when the AFP concentration was 10 ng/ml was 24,221 (RIU).

5.1.9. Experimental Example 3

CLEIA was conducted in the same manner as in Experimental Example 1 except that particles (iii) were used instead of particles (i) and magnetic separation was used for separation and washing of particles. The noise intensity of the sample which not containing AFP was 52 (RIU). The signal intensity of the sample when the AFP concentration was 10 ng/ml was 23,784 (RIU).

5.1.10. Comparative Experimental Example 1

CLEIA was conducted in the same manner as in Experimental Example 1 except that particles (i') were used instead of particles (i). The noise intensity of the sample which not containing AFP was 628 (RIU). The signal intensity of the sample when the AFP concentration was 10 ng/ml was 15,382 (RIU).

5.1.11. Comparative Experimental Example 2

100 µg of an antibody ("anti-AFP antibody" manufactured by Cosmo Bio Co., Ltd.) to human α-fetoprotein, which is a tumor marker, was added to a water dispersion of 10 mg of particles (ii') containing a glycidyl group as an active group, with a solid concentration of 1% and the mixture was reacted at room temperature for 18 hours. After the reaction, the particles were separated by centrifugation, repeatedly washed with a washing solution (25 mmol/l Tris-HCl, 7.4 pH, containing 0.01% Tween 20), and diluted with the washing solution to a particle concentration of 0.5% to obtain probe-bound particles (particles for immunoassay) with an anti-AFP antibody bound as a primary probe. The chemiluminescence enzyme immunity assay (CLEIA) was carried out using the probe-bound particles. The noise intensity of the sample which not containing AFP was 381 RIU (Relative intensity unit). The signal intensity of the sample when the AFP concentration was 10 ng/ml was 9,201 (RIU).

5.2. Example 2

5.2.1. Evaluation Method

5.2.1-1. Contact Angle of Dry Coating Film Obtained from Water Dispersion with Water 50 mg of the magnetic particles obtained in the later-described Synthesis Examples and Comparative Synthesis Examples were washed ten times with 1 ml of purified water and finally dispersed in 0.2 ml of purified water to prepare water dispersions. The water dispersions were applied to sheets of glass slide using an applicator and dried at a humidity of 40% and a temperature of 25° C. for 24 hours to obtain dry coating films. The contact angle of the dry coating films with water was measured using an FAMAS contact angle measurement system ("Drop Master 900" manufactured by Kyowa Interface Science Co., Ltd. according to the following method.

An image data of water drops was acquired from the horizontal direction using a camera at 0.15 seconds after dropping 1.0 µl of water drops onto the dry coating film to determine the contact angle of the dry coating film with water from the angle between the outline of the water drop and the horizon of the coating film, assuming that the outline of water drop is a part of a circle's perimeter.

5.2.1-2. Non-Specific Adsorption 0.5 ml of a phosphate buffer solution containing 1% bovine serum albumin (BSA) was added to 1 mg of each of magnetic particles obtained in the Synthesis Examples and Comparative Synthesis Examples, followed by mixing with inversion of the container at 25° C. for two hours. The magnetic particles were separated by magnetic separation and washed twice with a phosphate buffer solution. BSA non-specifically adsorbed in the magnetic particles were eluted with an aqueous solution of sodium dodecylsulfate (SDS), separated by SDS gel electrophoresis, and stained by silver staining to develop a color. A color of BSA of a known weight was also developed in the same gel. The colored gel was read into an imaging densitometer ("GS-700 manufactured by Bio-Rad Laboratories, Inc.) to determine the amount of BSA absorbed by magnetic particles.

5.2.1-3. Viscosity of Pellets 2 mg of magnetic particles were dispersed in a 0.5 ml of 0.1% Triton X-100 aqueous solution in a 1.5 ml plastic (polypropylene) tube ("Safe-lock tube" manufactured by Eppendorf Co., Ltd.). The tube was caused to vertically stand. Pellets were magnetically attracted by causing a neodium magnet with a surface magnetic flux density of 3,000 gauss to come in contact with the side wall of the tube for 30 seconds. The entire amount of the supernatant solution was removed from the bottom of the tube using a pipette. Pellets which did not flow down from the side wall of the tube when the magnet was separated (pellets with a moderate viscosity) were designated Pellets A, and those flown down from the side wall (pellets with too low a viscosity) were designated Pellets B (see Table 1).

5.2.2. Synthesis Example 4 (Most Preferable Constitution (1))

2 parts of 75% di(3,5,5-trimethylhexanoyl) peroxide solution ("Peroyl 355-75(S)" manufactured by NOF Corp.) in a hydrocarbon and 20 parts of 1% aqueous solution of sodium dodecylsulfate were mixed and finely emulsified using an ultrasonic dispersion equipment. The emulsion was added to a reactor containing 13 parts of polystyrene particles with a particle size of 0.77 µm and 41 parts of water and the mixture was stirred at 25° C. for 12 hours. In another vessel, 96 parts of styrene and 4 parts of divinylbenzene were emulsified in 400 parts of 0.1% aqueous solution of sodium dodecylsulfate. The resulting emulsion was added to the above reactor. After stirring at 40° C. for two hours, the mixture was heated to 75° C. and polymerized for 8 hours. After cooling to room temperature, particles were separated by centrifugation and washed with water. The average particle diameter was 1.5 µm. The particles were dried and ground to obtain nuclear particles.

Next, ferrite-type fine magnetic material particles (average primary particle diameter: 0.01 µm) with a hydrophobized surface were prepared by adding acetone to an oily magnetic fluid ("EXP series" manufactured by Ferrotec Corp.) to obtain a precipitate of the particles and drying the precipitate.

Then, 15 g of the nuclear particles and 15 g of the hydrophobized fine magnetic material particles were thoroughly mixed in a mixer. The mixture was processed by a hybridization system ("Type NHS-0" manufactured by Nara Machinery Co., Ltd.) at a peripheral speed of blades (stirring blades) of 100 n/sec (16,200 rpm) for 5 minutes to obtain complex particles (M-1) with a particle diameter of 1.6 µm, having a magnetic material layer formed on the outside of the nuclear particles.

A 1 l separable flask was charged with 750 g of an aqueous solution of 0.5 wt % of sodium dodecylbenzenesulfonate and 0.5 wt % of a nonionic emulsifying agent ("Emulgen 150" manufactured by Kao Corp.), followed by the addition of 30 g of the complex particles (M-1). The complex particles were dispersed using a homogenizer and heated to 70° C. Next, a pre-emulsion, prepared by dispersing 14 g of cyclohexyl methacrylate, 1 g of trimethylolpropane trimethacrylate, and 0.3 g of tert-butyl peroxy-2-ethylhexanoate ("Perbutyl O" manufactured by NOF Corp.) in 75 g of an aqueous solution of 0.5 wt % of sodium dodecylbenzenesulfonate and 0.5 wt % of a nonionic emulsifying agent ("Emulgen 150" manufactured by Kao Corp.), was dripped to the above 1 l separable flask controlled at 70° C. over one hour (a first coating layer).

Then, a pre-emulsion, prepared by dispersing 14 g of glycidyl methacrylate, 1 g of trimethylolpropane trimethacrylate, and 0.3 g of tert-butyl peroxy-2-ethylhexanoate ("Perbutyl O" manufactured by NOF Corp.) in 75 g of an aqueous solution of 0.5 wt % of sodium dodecylbenzenesulfonate and 0.5 wt % of a nonionic emulsifying agent ("Emulgen 150" manufactured by Kao Corp.), was dripped to the above 1 l separable flask controlled at 70° C. over one hour (a second coating layer). After heating to 80° C., the polymerization was continued for two hours before completing the reaction.

The resulting water dispersion of magnetic particles was purified by magnetism and gravity precipitation to obtain a water dispersion with a solid component concentration of 10%. The particle diameter of the resulting magnetic particles was 2.0 μm and the yield was about 50%. In addition, based on the fact that no glycidyl groups were observed in the reflective FT-IR spectrum of dry particle coating film, it was confirmed that glycidyl groups derived from glycidyl methacrylate used as a monomer were hydrolyzed. Because an alcoholic hydroxyl group is produced by the hydrolysis, it was confirmed that the coating layer of the magnetic particles of this Synthesis Example include a hydrophilic polymer part and the hydrophilic polymer part has an alcoholic hydroxyl group.

The contact angle of the dry coating film obtained from the water dispersion with water, the amount of non-specific adsorption, and the viscosity of pellets of the magnetic particles of this Synthesis Example were evaluated. The results are shown in Table 1.

5.2.3. Synthesis Example 5 (Most Preferable Constitution (2))

A 1 l separable flask was charged with 750 g of an aqueous solution of 0.25 wt % of sodium dodecylbenzenesulfonate and 0.25 wt % of a nonionic emulsifying agent ("Emulgen 150" manufactured by Kao Corp.), followed by the addition of 30 g of the complex particles (M-1) obtained in Synthesis Example 4. The complex particles were dispersed using a homogenizer and heated to 60° C. Then, a pre-emulsion, prepared by dispersing 30 g of cyclohexyl methacrylate, 1.2 g of tert-dodecanethiol, and 1.5 g of tert-butyl peroxy-2-ethylhexanoate ("Perbutyl O" manufactured by NOF Corp.) in 50 g of an aqueous solution of 0.5 wt % of sodium dodecylbenzenesulfonate and 0.5 wt % of a nonionic emulsifying agent ("Emulgen 150" manufactured by Kao Corp.), was dripped to the above 1 l separable flask controlled at 60° C. over two hours (a first coating layer).

Next, after cooling the reaction solution to room temperature, a pre-emulsion, prepared by dispersing 0.375 g of tert-butyl peroxy-2-ethylhexanoate ("Perbutyl O" manufactured by NOF Corp.) in 50 g of an aqueous solution of 0.5 wt % of sodium dodecylbenzenesulfonate and 0.5 wt % of a nonionic emulsifying agent ("Emulgen 150" manufactured by Kao Corp.), was added to the above 1 l separable flask and the mixture was stirred at room temperature for 15 hours. Then, a pre-emulsion, prepared by dispersing 2.25 g of methacrylic acid and 9.0 g of ethylene glycol dimethacrylate in 50 g of an aqueous solution of 0.5 wt % of sodium dodecylbenzenesulfonate and 0.5 wt % of a nonionic emulsifying agent ("Emulgen 150" manufactured by Kao Corp.), was added to the above 1 l separable flask which had been stirred at room temperature for 15 hours. The mixture was further stirred at room temperature for two hours. After heating the 1 l separable flask to 80° C., the polymerization was continued for further two hours before completing the reaction (a second coating layer).

The resulting water dispersion of magnetic particles was purified by magnetism and gravity precipitation to obtain a water dispersion of magnetic particles with a solid component concentration of 1%. The water dispersion was washed twice with 1 l of acetone. Then, the particles were dispersed in 1 l of acetone, followed by stirring for two hours, thereby causing the particles to come into contact with acetone (an organic solvent). In this manner, a part of the polymer part was eluted with acetone from the particles. The polymer part was then washed twice with 1 l of acetone and washed with water to remove acetone, thereby obtaining magnetic particles with porous surface.

The water dispersion of magnetic particles obtained in this Synthesis Example was purified by magnetism and gravity precipitation to obtain a water dispersion with a solid component concentration of 10%. The particle diameter of the magnetic particles obtained in this Synthesis Example was 2.2 μm and the yield was about 10%.

The contact angle of the dry coating film obtained from the water dispersion with water, the amount of non-specific adsorption, and the viscosity of pellets of the magnetic particles of this Synthesis Example were evaluated. The results are shown in Table 1.

5.2.4. Comparative Synthesis Example 3

A 1 l separable flask was charged with 750 g of an aqueous solution of 0.5 wt % of sodium dodecylbenzenesulfonate and 0.5 wt % of a nonionic emulsifying agent ("Emulgen 150" manufactured by Kao Corp.), followed by the addition of 30 g of the complex particles (M-1) obtained in Synthesis Example 4. The complex particles were dispersed using a homogenizer and heated to 70° C. Next, a pre-emulsion, prepared by dispersing 1 g of methacrylic acid, 15 g of styrene, and 0.3 g of tert-butyl peroxy-2-ethylhexanoate ("Perbutyl O" manufactured by NOF Corp.) in 75 g of an aqueous solution of 0.5 wt % of sodium dodecylbenzenesulfonate and 0.5 wt % of a nonionic emulsifying agent ("Emulgen 150" manufactured by Kao Corp.), was dripped to the above 1 l separable flask controlled at 70° C. over one hour. After heating to 80° C., the polymerization was continued for two hours before completing the reaction.

The water dispersion of magnetic particles obtained in this Comparative Synthesis Example was purified by magnetism and gravity precipitation to obtain a water dispersion with a solid component concentration of 10%. The particle diameter of the magnetic particles obtained in this Comparative Synthesis Example was 2.0 μm and the yield was about 50%.

The contact angle of the dry coating film obtained from the water dispersion with water, the amount of non-specific adsorption, and the viscosity of pellets of the magnetic particles obtained in this Comparative Synthesis Example were evaluated. The results are shown in Table 1.

5.2.5. Comparative Synthesis Example 4

A 1 l separable flask was charged with 750 g of an aqueous solution of 0.5 wt % of sodium dodecylbenzenesulfonate and 0.5 wt % of a nonionic emulsifying agent ("Emulgen 150" manufactured by Kao Corp.), followed by the addition of 30 g of the complex particles (M-1) obtained in Synthesis Example 4. The complex particles were dispersed using a homogenizer and heated to 70° C. Next, a pre-emulsion, prepared by dispersing 15 g of cyclohexyl methacrylate and 0.3 g of tert-butyl peroxy-2-ethylhexanoate ("Perbutyl O" manufactured by NOF Corp.) in 75 g of an aqueous solution of 0.5 wt % of sodium dodecylbenzenesulfonate and 0.5 wt % of a nonionic emulsifying agent ("Emulgen 150" manufactured by Kao Corp.), was dripped to the above 1 l separable flask controlled at 70° C. over one hour (a first coating layer).

Then, a pre-emulsion, prepared by dispersing 10 g of carboxymethylcellulose, 10 g of glycidyl methacrylate, and 0.3 g of tert-butyl peroxy-2-ethylhexanoate ("Perbutyl O" manufactured by NOF Corp.) in 75 g of an aqueous solution of 0.5 wt % of sodium dodecylbenzenesulfonate and 0.5 wt % of a nonionic emulsifying agent ("Emulgen 150" manufactured by Kao Corp.), was dripped to the above 1 l separable flask controlled at 70° C. over one hour (a second coating layer). After heating to 80° C., the polymerization was continued for two hours before completing the reaction.

The water dispersion of magnetic particles obtained in this Comparative Synthesis Example was purified by magnetism and gravity precipitation to obtain a water dispersion with a solid component concentration of 10%. The particle diameter of the magnetic particles obtained in this Comparative Synthesis Example was 2.1 μm and the yield was about 50%. Based on the fact that no glycidyl groups were observed in the reflective FT-IR spectrum of dry particle coating film, it was confirmed that glycidyl groups derived from glycidyl methacrylate used as a monomer were hydrolyzed.

The contact angle of the dry coating film obtained from the water dispersion with water, the amount of non-specific adsorption, and the viscosity of pellets of the magnetic particles obtained in this Comparative Synthesis Example were evaluated. The results are shown in Table 1.

TABLE 1

|  | Synthesis Example | | Comparative Synthesis Example | |
|---|---|---|---|---|
|  | 4 | 5 | 3 | 4 |
| Contact angle of a dry coating film with water | 15° | 32° | 115° | 4° |
| Amount of non-specific adsorption per 1 mg of magnetic particles | 20 ng | 50 ng | 1800 ng | 20 ng |
| Viscosity of pellets | A | A | A | B |

As shown in Table 1, the magnetic particles of Synthesis Examples 4 and 5 exhibited a small non-specific adsorptivity and produced pellets with a moderate viscosity, due to inclusion of the fine magnetic material particles and the polymer part containing a hydrophilic polymer part and a crosslinked polymer part and capability of a dry coating film obtained from the water dispersion thereof of exhibiting a contact angle with water of 5° to 60°.

On the other hand, the magnetic particles of Comparative Synthesis Example 3 of which the dry coating film has a contact angle of greater than 60° exhibited a great non-specific adsorptivity, and the magnetic particles of Comparative Synthesis Example 4 of which the dry coating film has a contact angle of less than 5° produced pellets having too low a viscosity to be maintained on the side of the tube.

5.3. Example 3

5.3.1. Evaluation Method
5.3.1-1. Signal Measurement by CLEIA (Chemiluminescence Enzyme Immunity Assay)

10 μl of particle dispersions (equivalent to 50 μg of particles) obtained in the later-described Synthesis Examples and Comparative Synthesis Examples, sensitized with an anti-AFP (α-fetoprotein) antibody, were taken in a test tube and mixed with 50 μl of a standard sample of an AFP antigen (manufactured by NIPPON BIOTEST LABO.) diluted to a concentration of 100 ng/ml with fetal calf serum (FCS). The mixture was reacted at 37° C. for 10 minutes. After magnetically separating the particles and after removing the supernatant liquid, 40 μl of an anti-AFP antibody (a reagent attached to "Lumipulse AFP-N" manufactured by Fujirebio Inc.), labeled with an alkali phophataze (ALP) as a secondary antibody, was added, followed by a reaction at 37° C. for 10 minutes. Next, after centrifugation to separate particles and removing the supernatant liquid, the resulting particles were washed three times by centrifugation using PBS and dispersed in 50 μl of 0.01% Tween 20. The resulting dispersion was transferred to a new tube. After the addition of 100 μl of an ALP substrate solution (Lumipulse substrate solution manufactured by Fujirebio Inc.), the mixture was reacted at 37° C. for 10 minutes to measure the amount of chemiluminescence. A chemiluminescence luminometer ("Lumat LB9507" manufactured by Berthold Japan, Co., Ltd.) was used for measuring the chemiluminescence.

5.3.1-2. Measurement of Noise

The amount of chemiluminescence as noise was measured in the same manner as the signal measurement by CLEIA (Chemiluminescence enzyme immunity assay) in 5.3.1-1. above, except that the dispersion of particles was not mixed with the standard sample.

5.3.1-3. Particle Size

The number average particle diameter of the particles and the coefficient of variation were measured using a laser diffraction particle size distribution analyzer ("SALD-200V" manufactured by Shimadzu Corp.).

5.3.2. Synthesis Example 6

2 parts by mass of 75% di(3,5,5-trimethylhexanoyl) peroxide solution ("Peroyl 355-75(S)" manufactured by NOF Corp.) and 20 parts by mass of 1% aqueous solution of sodium dodecylsulfate were mixed and finely emulsified using an ultrasonic dispersion equipment. The emulsion was added to a reactor containing 13 parts by mass of polystyrene particles with a particle size of 0.77 μm and 41 parts by mass of water and the mixture was stirred at 25° C. for 12 hours. In another vessel, 96 parts by mass of styrene and 4 parts by mass of divinylbenzene were emulsified in 400 parts by mass of 0.1% aqueous solution of sodium dodecylsulfate. The resulting emulsion was added to the above reactor. After stirring at 40° C. for two hours, the mixture was heated to 75° C. and polymerized for 8 hours. After cooling to room temperature, particles were separated by centrifugation, washed with water, dried, and ground to obtain core particles. The number average particle diameter of the core particles was 1.5 μm.

Next, ferrite-type fine magnetic material particles (average primary particle diameter: 0.01 μm) with a hydrophobized surface were prepared by adding acetone to an oily magnetic fluid ("EXP series" manufactured by Ferrotec Corp.) to obtain a precipitate of the particles and drying the precipitate.

Then, 15 g of the above core particles and 15 g of the above fine magnetic material particles were thoroughly mixed in a mixer. The mixture was processed by a hybridization system ("Type NHS-0" manufactured by Nara Machinery Co., Ltd.) at a peripheral speed of blades (stirring blades) of 100 n/sec (16,200 rpm) for 5 minutes to obtain mother particles with a number average particle diameter of 2.0 μm, having a magnetic material layer of fine magnetic material particles on the surface.

Next, a 1 l separable flask was charged with 375 g of an aqueous solution (hereinafter referred to as "aqueous solution of dispersion agent") of 0.25 wt % of sodium dodecylbenzenesulfonate and 0.25 wt % of a nonionic emulsifying agent ("Emulgen 150" manufactured by Kao Corp.), followed by the addition of 15 g of the mother particles having a magnetic material layer prepared above. The mother particles were dispersed using a homogenizer and heated to 60° C. A pre-emulsion, prepared by dispersing 27 g of methyl methacrylate, 3 g of trimethylolpropane trimethacrylate (TMP), and 0.6 g of di(3,5,5-trimethylhexanoyl) peroxide ("Peroyl 355" manufactured by NOF Corp.) in 150 g of the aqueous solution of dispersion agent, was dripped to the above 1 l separable flask controlled at 60° C. over one and half hours. After dripping and stirring for one hour while maintaining the mixture at 60° C., a pre-emulsion prepared by dispersing 13.5 g of glycidyl methacrylate (GMA), 1.5 g of TMP, and 0.3 g of di(3,5,5-trimethylhexanoyl) peroxide ("Peroyl 355" manufactured by NOF Corp.) in 75 g of the aqueous solution of dispersion agent was dripped to the above 1 l separable flask controlled at 60° C. over one and half hours. After heating to 75° C., the polymerization was continued for two hours before completing the reaction. Subsequently, 60 ml of 1 mol/l sulfuric acid was added to the 1 l separable flask and the mixture was stirred at 60° C. for six hours. The particles in the separable flask were magnetically separated and repeatedly washed with distilled water. Magnetic particles having a 2,3-dihydroxypropyl group (hereinafter indicated as "A-1 particles") were obtained in this manner.

Next, 1.0 g of dry particles obtained by drying the A-1 particles under vacuum were washed with 10 ml of pyridine and dispersed in 5 ml of pyridine. A solution of 3 g of succinic anhydride dissolved in 25 ml of pyridine was added to the resulting dispersion and the mixture was stirred at 60° C. for two hours. After the reaction, particles were magnetically separated and washed three times with acetone, three times with a 0.1 M aqueous solution of sodium hydroxide, and four times with distilled water to obtain carboxyl group-containing magnetic particles (hereinafter indicated as "B-1 particles"). The number average particle diameter of the carboxyl group-containing magnetic particles (B-1 particles) was 2.9 µm.

5.3.3. Synthesis Example 7

Carboxyl group-containing magnetic particles ("B-2 particles") were prepared in the same manner as in Synthesis Example 6, except for using 2-hydroxyethyl methacrylate instead of GMA and omitting the step of adding 60 ml of 1 mol/l sulfuric acid to the 1 l separable flask and stirring at 60° C. for six hours. The number average particle diameter of the carboxyl group-containing magnetic particles (B-2 particles) was 2.8 µm.

5.3.4. Comparative Synthesis Example 5

Magnetic particles ("B-3 particles") equivalent to A-1 particles were prepared in the same manner as in Synthesis Example 6, except for using 13.5 g of cyclohexyl methacrylate and 1.5 g of methacrylic acid instead of 13.5 g of GMA and 1.5 g of TMP and omitting the step of adding 60 ml of 1 mol/l sulfuric acid to the 1 l separable flask and stirring at 60° C. for six hours. The number average particle diameter of the resulting magnetic particles (B-3 particles) was 2.9 µm.

5.3.5. Experimental Examples 4 and 5

Probe-bound particles bound with an anti-AFP antibody were prepared as follows (Experimental Example 4). 5 mg of 1-ethyl-3-dimethylaminopropylcarbodiimide hydrochloride (manufactured by Dojindo Laboratories, Inc.) was dissolved in 1 ml of a water dispersion of B-1 particles with a solid component concentration of 1% and 0.1 ml of 0.1 mM HCl solution was added, followed by rotation stirring at room temperature for two hours. After further addition of 0.1 ml of a 0.1 mM HCl solution in which 100 µg of an anti-AFP antibody was dissolved, the mixture was stirred rotationally at room temperature for eight hours. Then, an operation of adding a phosphate buffer solution containing 0.1% bovine serum albumin (PBS, 0.1% BSA/PBS, pH=7.2) to magnetically separated particles, followed by magnetic separation of the particles was repeated three times to remove unreacted anti-AFP antibody. The signal of the resulting probe-bound particles was 157,705 and the noise was 71.

Probe-bound particles were obtained in the same manner using B-2 particles (Experimental Example 5). As a result of the same measurements as above, the resulting particles were confirmed to have a signal of 114,432 and the noise of 74.

5.3.6. Comparative Experimental Example 3

Probe-bound particles of Comparative Experimental Example 3 were obtained in the same manner as Experimental Example 4 except for using B-3 particles. The signal of the probe-bound particles of the Comparative Experimental Example 3 was 36,059 and the noise was 306.

As a result of the above experiments, the carboxyl group-containing particles obtained in Synthesis Examples 6 and 7 by a process including a step of producing an ester bond by the reaction of a hydroxyl group in organic polymer particles having the hydroxyl group with a carboxylic anhydride have been confirmed to exhibit high sensitivity and low noise as compared with particles prepared by a process not containing such a step in Comparative Synthesis Example 5.

5.4. Example 4

5.4.1. Evaluation Method 5.4.1-1. CLEIA (Chemiluminescence Enzyme Immunity Assay)

10 µl of organic polymer particle dispersions (equivalent to 50 µg particles) obtained in the later-described Examples and Comparative Examples, sensitized with an anti-AFP α-feto-protein) antibody, were taken in a test tube and mixed with 501 µl of a standard sample of an AFP antigen (manufactured by NIPPON BIOTEST LABO.) diluted to a concentration of 100 ng/ml with fetal calf serum (FCS). The mixture was reacted at 37° C. for 10 minutes. After separating particles magnetically or by centrifugation and after removing the supernatant liquid, 40 µl of an anti-AFP antibody (a reagent attached to "Lumipulse AFP-N" manufactured by Fujirebio Inc.), labeled with an alkali phophataze (hereinafter referred to as "ALP") as a secondary antibody, was added, followed by a reaction at 37° C. for 10 minutes. Next, after separating particles magnetically or by centrifugation and removing the supernatant liquid, the resulting particles were washed three times by centrifugation using a Trisbuffer/0.05% Tween 20 and dispersed in 50 µl of 0.01% Tween 20. The resulting dispersion was transferred to a new tube. After the addition of 100 µl of an ALP substrate solution (Lumipulse substrate solution manufactured by Fujirebio Inc.), the mixture was reacted at 37° C. for 10 minutes to measure the amount of chemiluminescence. A chemiluminescence luminometer ("Lumat LB9507" manufactured by Berthold Japan, Co., Ltd.) was used for measuring the chemiluminescence.

5.4.1-2. Particle Size

The number average particle diameter of the particles was measured using a laser diffraction particle size distribution analyzer ("SALD-200V" manufactured by Shimadzu Corp.).

5.4.2. Synthesis Example 8 (Synthesis of Organic Polymer Particles not Containing Magnetic Material)

Organic polymer particles (A) were prepared by the two-step swelling polymerization method using seed particles (mother particles) described below. Using polystyrene particles with a particle size of 0.98 µm obtained by soap-free polymerization as seed particles (mother particles), a water dispersion (solid component amount: 5.0 g) was prepared by dispersing these polystyrene particles in 500 g of water in nitrogen atmosphere. An organic solvent (0.1 g of "Shellsol TK") was added to and caused to be absorbed in the above water dispersion in the first step, and, in the second step, 2 g of polyoxyethylene methacryl ether having polyoxyethylene group recurring units (eight in average) of which the terminals are not substituted ("Blemmer PE-350" manufactured by NOF Corp., hereinafter referred to as "PE-350"), 38 g of methyl methacrylate (MMA), 10 g of ethylene glycol dimethacrylate, and 50 g of glycerol methacrylate (GLM) were added to and caused to be absorbed in the above water dispersion. Then, 2 g of AIBN (azobisisobutyronitrile) was added, and the mixture was slowly stirred at 75° C. for 24 hours. The reaction solution was cooled and filtered through a 500 mesh wire gauze to confirm that 99% of the product passed through the wire gauze. The polymerization stability was good. The polymerization yield was 99%. The organic polymer particles obtained by the above process are designated as particles (O-1).

Next, 5.0 g of O-1 particles were washed with distilled water by centrifugal separation and freeze dried to obtain dry particles. 1.0 g of the resulting dry particles was dispersed in 8 ml of pyridine and 0.2 g of p-toluenesulfonic acid chloride (Wako Pure Chemical Industries, Ltd.) was added. The mixture was stirred at room temperature for two hours. After the reaction, particles separated by using a centrifugal separator were collected and washed four times with acetone and four times with distilled water to obtain organic polymer particles for probe binding. (hereinafter indicated as "P-1"). The particle diameter of P—I particles was 2.6 µm.

5.4.3. Synthesis Example 9 (Synthesis of Organic Polymer Particles Containing Magnetic Material)

2 parts by mass of 75% di(3,5,5-trimethylhexanoyl) peroxide solution ("Peroyl 355-75(S)" manufactured by NOF Corp.) and 20 parts by mass of 1% aqueous solution of sodium dodecylsulfate were mixed and finely emulsified using an ultrasonic dispersion equipment. The emulsion was added to a reactor containing 13 parts by mass of polystyrene particles with a particle diameter of 0.77 µm and 41 parts by mass of water and the mixture was stirred at 25° C. for 12 hours. In another vessel, 96 parts by mass of styrene and 4 parts by mass of divinylbenzene were emulsified in 400 parts by mass of 0.1% aqueous solution of sodium dodecylsulfate. The resulting emulsion was added to the above reactor. After stirring at 40° C. for two hours, the mixture was heated to 75° C. and polymerized for 8 hours. After cooling to room temperature, particles were separated by centrifugation, washed with water, dried, and ground. The ground particles were used as nuclear particles (preparation of nuclear particles). The number average particle diameter was 1.5 µm.

Next, ferrite-type fine magnetic material particles (average primary particle diameter: 0.01 µm) with a hydrophobized surface were prepared by adding acetone to an oily magnetic fluid ("EXP series" manufactured by Ferrotec Corp.) to obtain a precipitate of the particles and drying the precipitate.

Then, 15 g of the above nuclear particles and 15 g of the hydrophobized fine magnetic material particles were thoroughly mixed in a mixer. The mixture was processed by a hybridization system ("Type NHS-0" manufactured by Nara Machinery Co., Ltd.) at a peripheral speed of blades (stirring blades) of 100 m/sec (16,200 rpm) for 5 minutes to obtain mother particles with a number average particle diameter of 2.0 µm, having a magnetic material layer of fine magnetic material particles on the surface.

A 1 l separable flask was charged with 375 g of an aqueous solution of 0.25 wt % of sodium dodecylbenzenesulfonate and 0.25 wt % of a nonionic emulsifying agent ("Emulgen 150" manufactured by Kao Corp.), followed by the addition of 15 g of the mother particles having a magnetic material layer prepared above. The mother particles were dispersed using a homogenizer and heated to 60° C. Next, a re-emulsion, prepared by dispersing 27 g of MMA, 3 g of trimethylolpropane trimethacrylate (TMP), and 0.6 g of di(3,5,5-trimethylhexanoyl) peroxide ("Peroyl 355" manufactured by NOF Corp.) in 150 g of an aqueous solution of 0.25 wt % of sodium dodecylbenzenesulfonate and 0.25 wt % of a nonionic emulsifying agent ("Emulgen 150" manufactured by Kao Corp.), was dripped to the above 1 l separable flask controlled at 60° C. over one hour and half. After dripping and stirring for one hour while maintaining the mixture at 60° C., a pre-emulsion prepared by dispersing 13.5 g of glycidyl methacrylate (GMA), 1.5 g of TMP, and 0.3 g of di(3,5,5-trimethylhexanoyl) peroxide ("Peroyl 355" manufactured by NOF Corp.) in 75 g of an aqueous solution of 0.5 wt % of a reactive surfactant having a polyoxyethylene group of which the terminal was replaced with a sulfonate group ("Aqualon KH-10" manufactured by Daiichi Kogyo Seiyaku Co., Ltd.) was dripped to the above 1 l separable flask controlled at 60° C. over one and half hours. After heating to 75° C., the polymerization was continued for two hours before completing the reaction. Subsequently, 60 ml of 1 mol/l sulfuric acid was added to a 1 l separable flask and the mixture was stirred at 60° C. for six hours. The particles in the separable flask were magnetically separated and repeatedly washed with distilled water. A dispersion of organic polymer particles containing magnetic material was thus prepared (hereinafter indicated as "O-2").

Next, 1.0 g of dry particles obtained by freeze drying the O-2 particles were dispersed in 8 ml of pyridine and 0.2 g of p-tosyl chloride was added. The mixture was stirred at room temperature for two hours. After the reaction, particles were magnetically separated and washed four times with acetone and four times with distilled water to obtain organic polymer particles for probe binding. (hereinafter indicated as "P-2 particles"). The number average particle diameter of the P-2 particles was 2.9 µm.

5.4.4. Synthesis Example 10 (Synthesis of Probe-Bound Particles not Containing Magnetic Material)

10 mg of the organic polymer particles for probe binding. (P-1 particles) obtained in Synthesis Example 8 was dispersed in 1.0 ml of a boric acid buffer solution (0.1 mol/l, pH=9.5). 100 µg of an antibody ("anti-AFP antibody" manufactured by Cosmo Bio Co., Ltd.) to human α-fetoprotein (AFP), which is a tumor marker, was added and reacted at room temperature for 18 hours. Particles were excellently dispersed during the reaction. After the reaction, the particles were separated by centrifugation, repeatedly washed with a washing solution (25 mmol/l Tris-HCl, 7.4 pH, containing 0.01% Tween 20), and diluted with the washing solution to a particle concentration of 0.5% to obtain a dispersion of probe-bound particles ("Q-1 particles) sensitized with an anti-AFP antibody.

5.4.5. Synthesis Example 11 (Synthesis of Probe-Bound Particles Containing Magnetic Material)

A dispersion of probe-bound particles ("Q-2 particles) sensitized with an anti-AFP antibody was obtained in the same manner as in Synthesis Example 10, except that the organic polymer particles for probe binding. containing magnetic materials ("P-2 particles") prepared in Synthesis Example 9 were used instead of the organic polymer particles for probe binding. ("P-1 particles") and magnetic separation was used instead of centrifugal separation. Particles were excellently dispersed during the reaction.

5.4.6. Comparative Synthesis Example 6 (Synthesis of Probe-Bound Particles not Containing Magnetic Material)

10 mg of organic polymer particles for probe binding. (P-3 particles) obtained in the same manner as in Synthesis Example 8 except for not using PE-350 were dispersed in 1.0 ml of a boric acid buffer solution (0.1 mol/l, pH=9.5). 100 μg of an antibody ("anti-AFP antibody" manufactured by Cosmo Bio Co., Ltd.) to human α-fetoprotein (AFP), which is a tumor marker was added to the dispersion and reacted at room temperature for 18 hours. Particles were not excellently dispersed during the reaction. After the reaction, the particles were separated by centrifugation, repeatedly washed with a washing solution (25 mmol/l Tris-HCl, 7.4 pH, containing 0.01% Tween 20), and diluted with the washing solution to a particle concentration of 0.5% to obtain a dispersion of probe-bound particles ("Q-3 particles) sensitized with an anti-AFP antibody.

5.4.7. Comparative Synthesis Example 7 (Synthesis of Probe-Bound Particles Containing Magnetic Material)

Organic polymer particles for probe binding. ("P-4 particles") containing a magnetic material was obtained in the same manner as in Synthesis Example 9, except for using 2-hydroxyethyl methacrylate instead of GMA. A dispersion of probe-bound particles ("Q-4") sensitized with an anti-AFP antibody was obtained in the same manner as in Synthesis Example 10, except for using the organic polymer particles (P-4 particles) for probe binding. containing a magnetic material instead of the organic polymer particles (P-1 particles) for probe binding, and employing magnetic separation instead of centrifugal separation. Particles were excellently dispersed during the reaction.

5.4.8. Experimental Example 6

The chemiluminescence enzyme immunity assay (CLEIA) was carried out using a dispersion of the probe-bound particles (Q-1) containing no magnetic material obtained in Synthesis Example 10. The noise intensity of the sample which not containing AFP was 158 RIU (Relative intensity unit). The signal intensity of the sample when the AFP concentration was 100 ng/ml was 140,997 (RIU).

5.4.9. Experimental Example 7

CLEIA was conducted in the same manner as in Example 1 except for using a dispersion in which the probe-bound particles (Q-2) containing a magnetic material obtained in Synthesis Example 11 instead of the dispersion of the probe-bound particles (Q-1). The noise intensity of the sample which not containing AFP was 60 (RIU). The signal intensity of the sample when the AFP concentration was 100 ng/ml was 195,038 (RIU).

5.4.10. Comparative Experimental Example 4

CLEIA was conducted in the same manner as in Experimental Example 6 except for using a dispersion of the probe-bound particles (Q-3) not containing a magnetic material obtained in Comparative Synthesis Example 6 instead of the dispersion of the probe-bound particles (Q-1). The noise intensity of the sample which not containing AFP was 142 (RIU). The signal intensity of the sample when the AFP concentration was 100 ng/ml was 106,351 (RIU).

As can be seen from the results of this Comparative Experimental Example, due to absence of polyoxyethylene groups, the particles (Q-3) obtained in the Comparative Synthesis Example 6 exhibited poor dispersibility during the reaction of the anti-AFP antibody, which is a probe, and a part of the particles agglomerated. Based on the above result, the particles (Q-3) obtained in the Comparative Synthesis Example 6 exhibited poor dispersibility due to the absence of polyoxyethylene groups, giving rise to low reactivity of the particles (Q-3) with a probe. For this reason, the signal strength obtained by using the particles (Q-3) is thought to be lower than the signal strength obtained by using the particles (Q-1).

5.4.11. Comparative Experimental Example 5

CLEIA was conducted in the same manner as in Experimental Example 6 except for using a dispersion of the probe-bound particles (Q-4) containing a magnetic material obtained in Comparative Synthesis Example 7 instead of the dispersion of the probe-bound particles (Q-1). The noise intensity of the sample which not containing AFP was 258 (RIU). The signal intensity of the sample when the AFP concentration was 100 ng/ml was 67,293 (RIU).

The particles (Q-4) obtained in Comparative Synthesis Example 7 exhibited a high noise and an low signal due to the absence of 2,3-dihydroxypropyl groups. Based on this result, the particles containing no 2,3-dihydroxypropyl groups such as particles (Q-4) are thought to exhibit a low reactivity with a probe and low reaction specificity.

What is claimed is:

1. Organic polymer particles, comprising:
   a carboxyl group; and
   a 2,3-dihydroxypropyl group;
   wherein said organic polymer particles are separated and dispersed particles;
   wherein the amount of the carboxyl group per the amount of solid components of said organic polymer particles is 5 to 100 μmol/g; and
   wherein a dry coating film obtained from a water dispersion of said organic polymer particles has a contact angle with water of 60° or less.

2. The organic polymer particles as defined in claim 1, further comprising superparamagnetic fine particles.

3. The organic polymer particles as defined in claim 2, further comprising:
   nuclear particles;
   a magnetic material layer comprising the superparamagnetic fine particles, said magnetic material layer being provided in the outer layer of the nuclear particles; and
   a polymer part having a carboxyl group and 2,3-dihydroxypropyl group, said polymer part being provided in the outer layer of the magnetic material layer.

4. The organic polymer particles as defined in claim 1, wherein said carboxyl group is obtained by hydrolysis of a monomer (A) in which the carboxyl group is protected by a protecting group.

5. The organic polymer particles as defined in claim 4, wherein said monomer (A) is (A-1) an ester monomer in which the carboxyl group of is protected by a tertiary alcohol.

6. The organic polymer particles as defined in claim 4, wherein said monomer (A) is (A-2) a cyclic ester monomer obtained by internal condensation of a monomer having a carboxyl group and a hydroxyl group in one molecule.

7. The organic polymer particles as defined in claim 4, wherein said monomer (A) is (A-3) an acid anhydride of a monomer having a carboxyl group.

8. The organic polymer particles as defined in claim 1, wherein a number average particle diameter of said organic particles is 1 to 10 μm.

9. A probe, comprising:
   the organic polymer particles as defined in claim 1 being bound to said probe.

10. Organic polymer particles, comprising:
    a carboxyl group; and
    a 2,3-dihydroxypropyl group;
    wherein said organic polymer particles comprise a polymer part which comprises an ester bond and a functional group having a carboxylic group on a surface of the organic polymer particles;

wherein the ester bond is obtained by reacting a hydroxyl group of the organic polymer particles with a carboxylic anhydride;

wherein said organic polymer particles are separated and dispersed particles;

wherein a dry coating film obtained from a water dispersion of said organic polymer particles has a contact angle with water of 60° or less;

wherein the amount of the carboxyl group per the amount of solid components of said organic polymer particles is 5 to 100 μmol/g.

* * * * *